US012617816B2

(12) United States Patent
Elliott

(10) Patent No.: US 12,617,816 B2
(45) Date of Patent: May 5, 2026

(54) COMPOSITION AND METHOD FOR IN VIVO ASSAY OF OPIOID RECEPTORS

(71) Applicant: THE TRUSTEES OF DARTMOUTH COLLEGE, Hanover, NH (US)

(72) Inventor: Jonathan T. Elliott, Meriden, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 854 days.

(21) Appl. No.: 17/776,242

(22) PCT Filed: Nov. 11, 2020

(86) PCT No.: PCT/US2020/060035
§ 371 (c)(1),
(2) Date: May 12, 2022

(87) PCT Pub. No.: WO2021/096971
PCT Pub. Date: May 20, 2021

(65) Prior Publication Data

US 2023/0021681 A1 Jan. 26, 2023

Related U.S. Application Data

(60) Provisional application No. 62/933,644, filed on Nov. 11, 2019.

(51) Int. Cl.
*C07K 7/06* (2006.01)
*A61K 31/485* (2006.01)
*A61K 49/00* (2006.01)

(52) U.S. Cl.
CPC .............. *C07K 7/06* (2013.01); *A61K 31/485* (2013.01); *A61K 49/0045* (2013.01)

(58) Field of Classification Search
CPC ........................................................ C07K 7/06
See application file for complete search history.

(56) References Cited

U.S. PATENT DOCUMENTS

| | | | |
|---|---|---|---|
| 2002/0064794 A1 | 5/2002 | Leung et al. | |
| 2003/0148291 A1 | 8/2003 | Robotti | |
| 2014/0127717 A1 | 5/2014 | Diwu et al. | |
| 2018/0371542 A1 | 12/2018 | Anton | |

FOREIGN PATENT DOCUMENTS

EP 3315531 B1 * 11/2019 ............ A61K 47/10

OTHER PUBLICATIONS

Feng et al (ACS Appl. Mater. Interfaces 2018, 10, 4359-4368 hereafter Feng) (Year: 2018).*

Nguyen et al (Brain Research 1590, 2014, 10-19 hereafter Nguyen) (Year: 2014).*

Samkoe et al (Cancer Control, vol. 25 (1), 2018 hereafter Samkoe) (Year: 2018).*

Bell et al., "Medication Treatment of Opioid Use Disorder," Biological Psychiatry, Jan. 1, 2020, pp. 82-88.

Belzeaux et al., "Focusing on the opioid system for addiction biomarker discovery" Trends in Molecular Medicine, vol. 24, No. Feb. 2, 2018, pp. 207-220.

Carr et al., "Using the shortwave infrared to image middle ear pathologies," Proceedings of the National Academy of Sciences vol. 113, No. 36 Sep. 6, 2016, pp. 9989-9994.

Christenson et al., "Two Cases of Sudden Sensorineural Hearing Loss After Methadone Overdose," Annals of Pharmacotherapy, vol. 44, Jan. 2010, pp. 207-210.

Davis et al., "Dynamic dual-tracer MRI-guided fluorescence tomography to quantify receptor density in vivo" Proceedings of the National Academy of Sciences, vol. 110, No. 22, May 28, 2013, pp. 9025-9030.

Deas et al., "Naltrexone treatment of adolescent alcoholics: an open-label pilot study" Journal of Child & Adolescent Psychopharmacology, vol. 15, No. 5, 2005, pp. 723-728.

Elliott et al., "Direct Characterization of Arterial Input Functions by Fluorescence Imaging of Exposed Carotid Artery to Facilitate Kinetic Analysis," Molecular Imaging and Biology, vol. 16, Jan. 14, 2014, pp. 488-494.

Elliott et al., "Image-derived arterial input function for quantitative fluorescence imaging of receptor-drug binding in vivo," Journal of Biophotonics, vol. 9, No. 3, 2016, Sep. 9, 2015, pp. 282-295.

Elliott et al., "Microdose fluorescence imaging of ABY-029 on an operating microscope adapted by custom illumination and imaging modules" Biomedical Optics Express, vol. 7, No. 9, Sep. 2016, pp. 3280-3288.

Elliott et al., "simultaneous in vivo fluorescent markers for perfusion, protoporphyrin metabolism, and egfr expression for optically guided identification of orthotopic glioma" Clinical Cancer Research, May 2017. vol. 23(9), pp. 2203-2212.

Fishman et al., "Treatment of opioid dependence in adolescents and young adults with extended release naltrexone: Preliminary case-series and feasibility," Addiction vol. 105, 2010, pp. 1669-1676.

Freeman et al., :The association of codeine, macrocytosis and bilateral sudden or rapidly progressive profound sensorineural deafness, Acta oto-laryngologica, vol. 129, 2009, pp. 1061-1066.

Frost et al., "Multicompartmental analysis of [11C]-carfentanil binding to opiate receptors in humans measured by positron emission tomography," Journal of Cerebral Blood Flow & Metabolism, vol. 9, 1989, pp. 398-409.

Greenwald MK, et al., "Buprenorphine maintenance and mu-opioid receptor availability in the treatment of opioid use disorder: implications for clinical use and policy" Drug Alcohol Dependence, Nov. 2014, vol. 144. 11 pages.

(Continued)

*Primary Examiner* — Micah Paul Young
(74) *Attorney, Agent, or Firm* — Cozen O'Connor

(57) ABSTRACT

Compositions and methods are provided to determine occupancy level of opioid receptors in a subject. The disclosed methods may be performed non-invasively in the inner ear of the subject, and may be performed at a point-of-care location to provide guidance to a practitioner on tapering on pharmacotherapy or on a patient's risk of relapse for substance abuse.

25 Claims, 10 Drawing Sheets

Specification includes a Sequence Listing.

(56) References Cited

OTHER PUBLICATIONS

Greenwald et al., "Effects of Buprenorphine Maintenance Dose on m-Opioid Receptor Availability, Plasma Concentrations, and Antagonist Blockade in Heroin-Dependent Volunteers" Neuropsychopharmacology, Nov. 2003, vol. 28, pp. 2000-2009.
Harell M. et al., "Total deafness with chronic propoxyphene abuse", The Laryngoscope. Sep. 1978, vol. 88 (9), pp. 1518-1521.
Ho T. et al., "Hydrocodone use and sensorineural hearing loss" Pain Physician, May 2007, vol. 10, pp. 467-472.
Iqbal N. "Recoverable hearing loss with amphetamines and other drugs", Journal of Psychoactive Drugs, Jun. 2004, vol. 36(2), pp. 285-288.
Ishiyama et al., "Heroin-induced reversible profound deafness and vestibular dysfunction", Addiction. Sep. 2001, vol. 96(9), pp. 1361-1364.
Johansson J et al., "Intranasal naloxone rapidly occupies brain mu-opioid receptors in human subjects" Neuropsychopharmacology: official publication of the American College of Neuropsychopharmacology, Mar. 2019, vol. 447 pages.
Lammertsma AA. et al., "Simplified Reference Tissue Model for PET Receptor studies" Neuroimage, Dec. 1996, vol. 4, No. 0066, pp. 153-158.
Liu JT. et al., "Quantifying Cell-Surface Biomarker Expression In Thick Tissues With Ratiometric Three-Dimensional Microscopy" Biophysical Journal, Mar. 2009, vol. 96, pp. 2405-2414.
Logan J. et al., "Distribution Volume Ratios Without Blood Sampling From Graphical Analysis of Pet Data" Journal of Cerebral Blood Flow & Metabolism, Sep. 1996, vol. 16, No. 5, pp. 834-840.
Mintun MA, et al., "A Quantitative Model for The In Vivo Assessment of Drug Binding Sites With Positron Emission Tomography" Annals of Neurology: Official Journal of the American Neurological Association and the Child Neurology Society, Mar. 1984, vol. 15(3), pp. 217-227.
Newman LC. et al., "Selective opioid agonist and antagonist competition for [311]-naloxone binding in amphibian spinal cord" Brain Research, 2000, vol. 884, pp. 184-191.
Nguyen KD. et al., "Mu-opioid receptor (MOR) expression in the human spiral ganglia" Brain Research, 1590, Nov. 2014, pp. 10-19.
Oh AK et al., "Deafness associated with abuse of hydrocodone/acetaminophen" Neurology. Jun. 27, 2000, vol. 54 No. 12, pp. 2345-2643.
Patrick SW. et al. "Prescription Opioid Epidemic and Infant Outcomes" Pediatrics, May 2015, vol. 135(5), pp. 842-850.
Pogue BW, et al. "Imaging targeted-agent binding in vivo with two probes" Journal of Biomedical Optics, May/Jun. 2010, vol. 15(3), 3 pages.
Rigby et al., "Profound Hearing Loss Associated With Oxycodone-Acetaminophen Abuse" Journal of Otolaryngology-Head & Neck Surgery, Dec. 2008, vol. 37 No. 6, pp. E161-162.
Rzasa Lynn R. et al. "Naloxone dosage for opioid reversal: current evidence and clinical Implications" Therapeutic Advances in Drug Safety, 2018, vol. 9(1), pp. 63-88.
Samkoe KS. et al., "Quantitative in vivo immunohistochemistry of epidermal growth factor receptor using a receptor concentration imaging approach" Cancer Research, Dec. 15, 2014, vol. 74(24), pp. 7465-7474.
Schrock A. et al., "Sudden sensorineural hearing loss after heroin injection" European Archives of Oto-Rhino-Laryngology, May 2008, vol. 265, pp. 603-606.
Tichauer KM. et al., Microscopic lymph node tumor burden quantified by macroscopic dual-tracer molecular imaging, Nature Medicine, Nov. 2014, vol. 20(11), pp. 1348-1356.
Tichauer KM. et al., "In Vivo Quantification of Tumor Receptor Binding Potential With Dual-Reporter Molecular Imaging" Molecular Imaging and Biology, 2012, vol. 14, pp. 584-592.
Tichauer KM. et al., "Improved tumor contrast achieved by single time point dual-reporter fluorescence imaging" Journal of Biomedical Optics, Jun. 2012, vol. 17(6), 11 pages.
Trescot AM. et al., "Opioid Pharmacology" Pain Physician, Mar. 2008, Opioid Special Issue: 11:S133-S153, 22 pages.
Van Gaalen FA et al., "Sudden hearing loss after a methadone overdose" European Archives of Oto-Rhino-Laryngology, 2009, pp. 773-774.
Zubieta JK. et al., "Buprenorphine-Induced Changes in Mu-Opioid Receptor Availability in Male Heroin-Dependent Volunteers: A Preliminary Study" Neuropsychopharmacology, 2000, vol. 23 No. 3, pp. 326-335.
International Patent Application No. PCT/US2020/060035 International Search Report and Written Opinion dated Mar. 30, 2021, 8 pages.

* cited by examiner

COMPOSITION AND METHOD FOR IN VIVO ASSAY OF OPIOID RECEPTORS

CROSS-REFERENCE TO RELATED APPLICATION

This application is a 35 U.S.C. § 371 filing of International Application No. PCT/US2020/060035 filed Nov. 11, 2020, which claims benefit of priority to U.S. Provisional Patent Application No. 62/933,644 filed on Nov. 11, 2019, which is incorporated herein by reference in its entirety.

GOVERNMENT RIGHTS

This invention was made with government support under grant number R21 EB024771 awarded by the National Institutes of Health. The government has certain rights in the invention.

FIELD

The present disclosure relates to compositions and methods for in vivo determination of mu-opioid receptor expression and activity for the prevention, diagnosis and treatment of opioid use disorder (OUD).

BACKGROUND

Opioid is currently an important point for managing clinically significant pain. Opioid receptors (OR) are abundant in the central nervous system and the peripheral nervous system. Activation of opioid receptors is useful clinically to produce analgesia; however, agonists such as morphine, fentanyl and its derivatives, and heroin, produce chemical dependence, a condition termed opioid use disorder (OUD). Deaths caused by OUD and opioid overdose now exceed those caused by motor vehicle accidents. Stratifying patients according to risk of opioid abuse remains a challenge. Preventing misuse/recreational use leading to the addiction cycle, improving abstinence/drug substitution (medical-treatment for opioid use disorder, or MOUD) and preventing relapse, overdose, and death remain an important societal and medical goal.

One of the major challenges of treating OUD is that there is no 'one-size-fits-all' approach. There is currently no methodology to predict which patient will do best with which medication (Bell and Strang, 2019). Data on opioid receptor expression and activity would help clinician in diagnosing and treating opioid use disorder. However, no in vivo non-invasive methods are currently available for measuring the expression and activity of opioid receptors.

SUMMARY

In one embodiment, the disclosure provides at least one probe that specifically binds to an opioid receptor (OR) in a subject, such as a human. In another embodiment, the probe contains the compound of formula (I) or a salt thereof. In one aspect, the salt is a pharmaceutically acceptable salt. In another aspect, the probe is non-antigenic. In another aspect, the amount of the probe does not cause significant toxic side effect and is safe for human.

Formula (I)

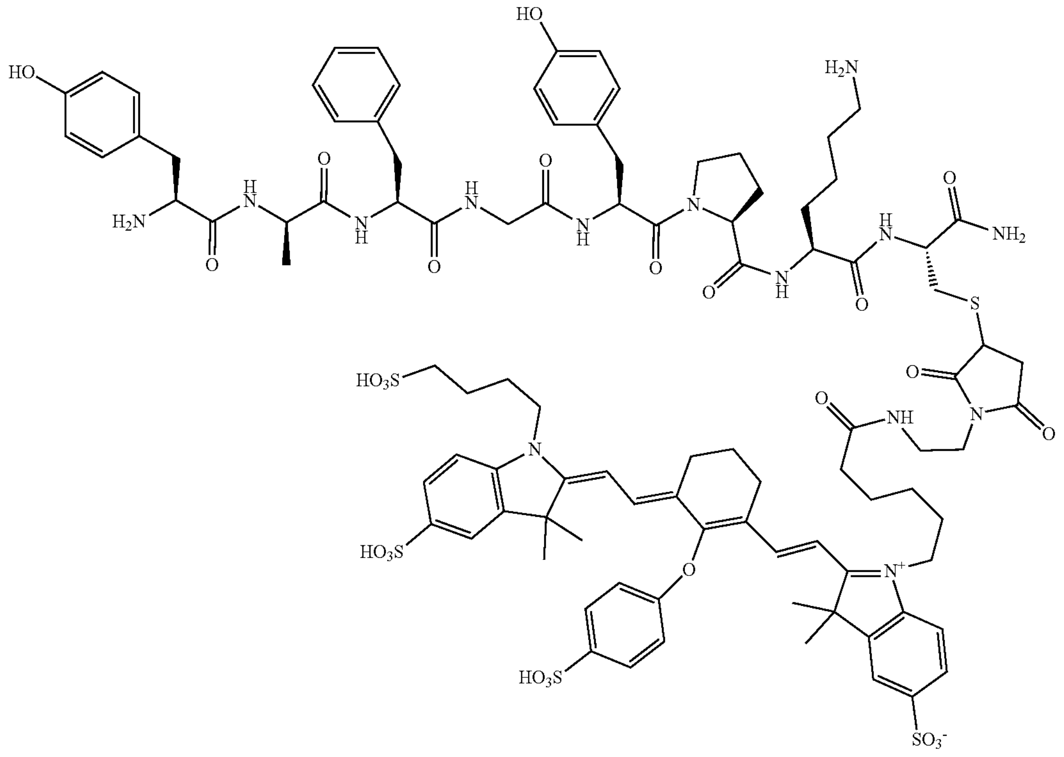

In one embodiment, the disclosure provides a composition including compound of formula (I) or a salt thereof. This compound of Formula (I) is a novel fluorescent peptide (also referred to as [Lys7]dermorphin-IRDye800CW or DRM-800). In another embodiment, the composition also contains a carrier. In some embodiments, the carrier is a pharmaceutically acceptable carrier. In another embodiment, the compound is prepared by solid phase peptide synthesis (SPPS) or by recombinant DNA methods. In another embodiment, the compound is prepared by an Fmoc-based solid-phase peptide synthesis (SPPS).

In one embodiment, the disclosed compositions and methods may be used to measure occupancy level of the opioid receptor in vivo in a subject by using the non-invasive methods described herein. In another embodiment, the disclosed compositions and methods may be used to measure occupancy level of the opioid receptor in vitro by using a sample taken from the subject.

In some aspects, the disclosure provides a method of determining occupancy level of an opioid receptor in a subject, including the steps of: (a) contacting at least one probe with the subject, wherein the probe binds specifically to the opioid receptor (OR) (b) measuring intensity of fluorescent signal emitted by the probe from inner ear of the subject; and (c) determining the occupancy level of the opioid receptor in the subject based on the fluorescence intensity.

In one embodiment, the opioid receptor is mu opioid receptor.

In one embodiment, step (b) above is performed non-invasively. In another embodiment, fluorescence intensity in spiral ganglion is measured in step (b). In another embodiment, fluorescence intensity is measured by using an oto-spectroscope.

In one embodiment, one probe is used. In another embodiment, two or more different probes are used simultaneously. In one aspect, the excitation wavelength used in step (b) ranges between 635 nm and 760 nm. In another aspect, the excitation wavelength is at or about 635 nm. In another aspect, the excitation wavelength is at or about 760 nm. In another aspect, two or more different excitation wavelengths are used simultaneously or sequentially.

In another embodiment, occupancy level of the opioid receptor in the subject is calculated quantitatively in step (c). In another embodiment, higher fluorescence intensity indicates lower occupancy level of the opioid receptor.

In another embodiment, the probe binds to the opioid receptor and is internalized inside the cells. In one aspect, the disclosed method may further include a step of measuring the rate of internalization of the probe. The occupancy level of the opioid receptor and the rate of internalization of the probe retrieved according to the methods described herein may be used to evaluate a subject's risk of developing an opioid use disorder in the future.

In one embodiment, the disclosure provides a method for determining the level of an opioid receptor in a sample of tissue or cells from a subject, including the steps of: contacting the sample with compound of formula (I) or a salt thereof; removing unbound compound of formula (I) from the sample; evaluating the bonding of the compound of formula (I) with the opioid receptor by detecting fluorescence intensity of the sample; and thereby determining the level of the opioid receptor in the sample. In some embodiments, the method further includes administering an effective amount of an opioid antagonist to the subject based on the level of the opioid receptor in the sample.

In another embodiment, the disclosure provides a method of preventing/treating opioid use disorder (OUD) in a subject, including the steps of: contacting a sample from the subject with compound of formula (I) or a salt thereof; removing unbound compound of formula (I) from the sample; evaluating the bonding of the compound of formula (I) with an opioid receptor by detecting fluorescence intensity of the sample; determining the level of the opioid receptor in the sample; and administering an effective amount of an opioid antagonist to the subject based on the level of the opioid receptor in the sample.

In another embodiment, the disclosure provides a method for detecting opioid use disorder (OUD) in a subject, including the steps of: contacting a sample from the subject with compound of formula (I) or a salt thereof; removing unbound compound of formula (I) from the sample; evaluating the bonding of the compound of formula (I) with an opioid receptor by detecting fluorescence intensity of the sample; determining the level of the opioid receptor in the sample; and determining whether is the subject is subjected to opioid user disorder based on the level of the opioid receptor.

In another embodiment, the disclosure provides a method for reducing the risk associated with the administration of an opioid antagonist in patients with opioid use disorder, including the steps of: contacting a sample from the subject with compound of formula (I) or a salt thereof; removing unbound compound of formula (I) from the sample; evaluating the bonding of the compound of formula (I) with an opioid receptor by detecting fluorescence intensity of the sample; determining the level of the opioid receptor in the sample; and administering an effective amount of an opioid antagonist to the subject based on the level of the opioid receptor in the sample.

In another embodiment, the disclosure provides a method of monitoring the response of a subject being treated with an opioid antagonist, including the steps of: determining the level of an opioid receptor in a first sample using a compound of formula (I), wherein the first sample is from the subject prior to treatment with the opioid antagonist using a compound of formula (I); and determining the level of the opioid receptor in a second sample using a compound of formula (I), wherein the second sample is from the subject after treatment with the opioid antagonist.

In some embodiments, the sample is from peripheral nervous system. In some embodiments, the sample is from inner ear of a subject.

In some embodiments, the subject is a mammal. In some embodiments, the subject is human.

In some embodiments, the method may further include a step (d) of administering an effective amount of an opioid antagonist or a partial opioid agonist to the subject based on the occupancy level of the opioid receptor in the subject. In some other embodiments, the opioid antagonist is selected from the group consisting of alvimopan, norbinaltorphimine, nalmefene, naloxone, naltrexone, methylnaltrexone, and nalorphine, and pharmaceutically acceptable salts or prodrugs thereof. In some embodiments, the amount of the opioid antagonist or the partial opioid agonist administered is determined based on the occupancy level of the opioid receptor in the subject. In some embodiments, the probe is administered by a means such as nasal spray, intravenous (IV) injection, oral administration or skin patch.

In some embodiments, the subject has been treated with a pain medication prescribed by a physician prior to step (a) above.

In some embodiments, the method is used for determining the dose of pharmacotherapy in the treatment of substance use disorder, such as an opioid use disorder (OUD), or is used to taper down the dose of pharmacotherapy.

In some embodiments, the subject is a pregnant woman with a substance use disorder and the disclosed method is used to reduce the risk of relapse in the subject.

In another aspect, the disclosure provides a kit for detecting an opioid receptor in a bodily sample taken from a subject, including a predetermined amount of compound of formula (I); and direction for use of the kit.

BRIEF DESCRIPTION OF THE DRAWINGS

The following figures form part of the present specification and are included to further illustrate aspects of the present disclosure.

DETAILED DESCRIPTION

Figure 1:
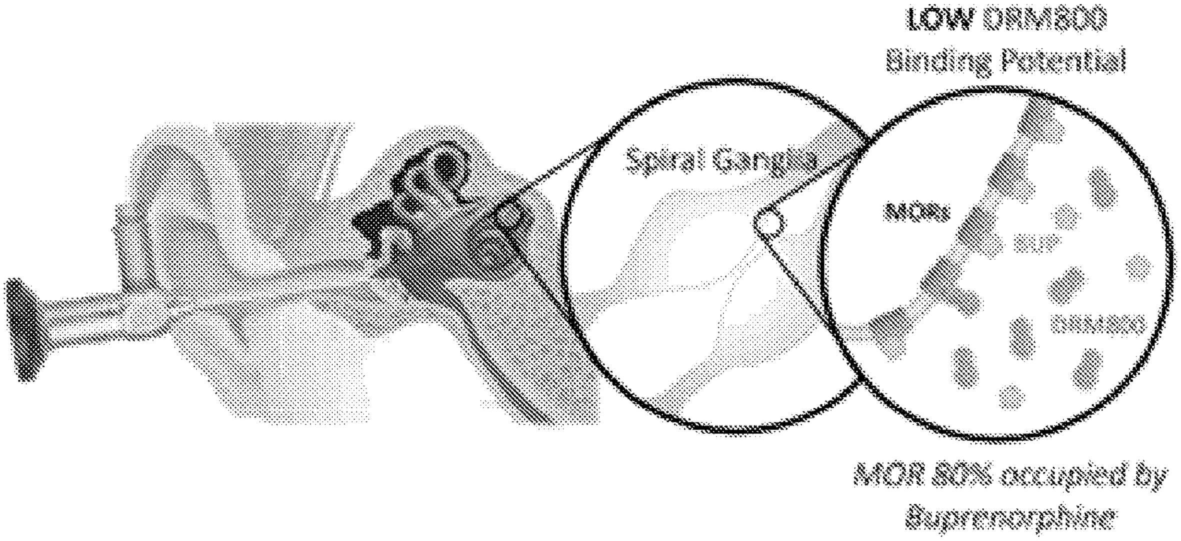
FIG. 1 illustrates how measurement is acquired aurally by interrogating the spiral ganglia to determine the mu-opioid receptor availability following a dose of buprenorphine.
Figure 2:
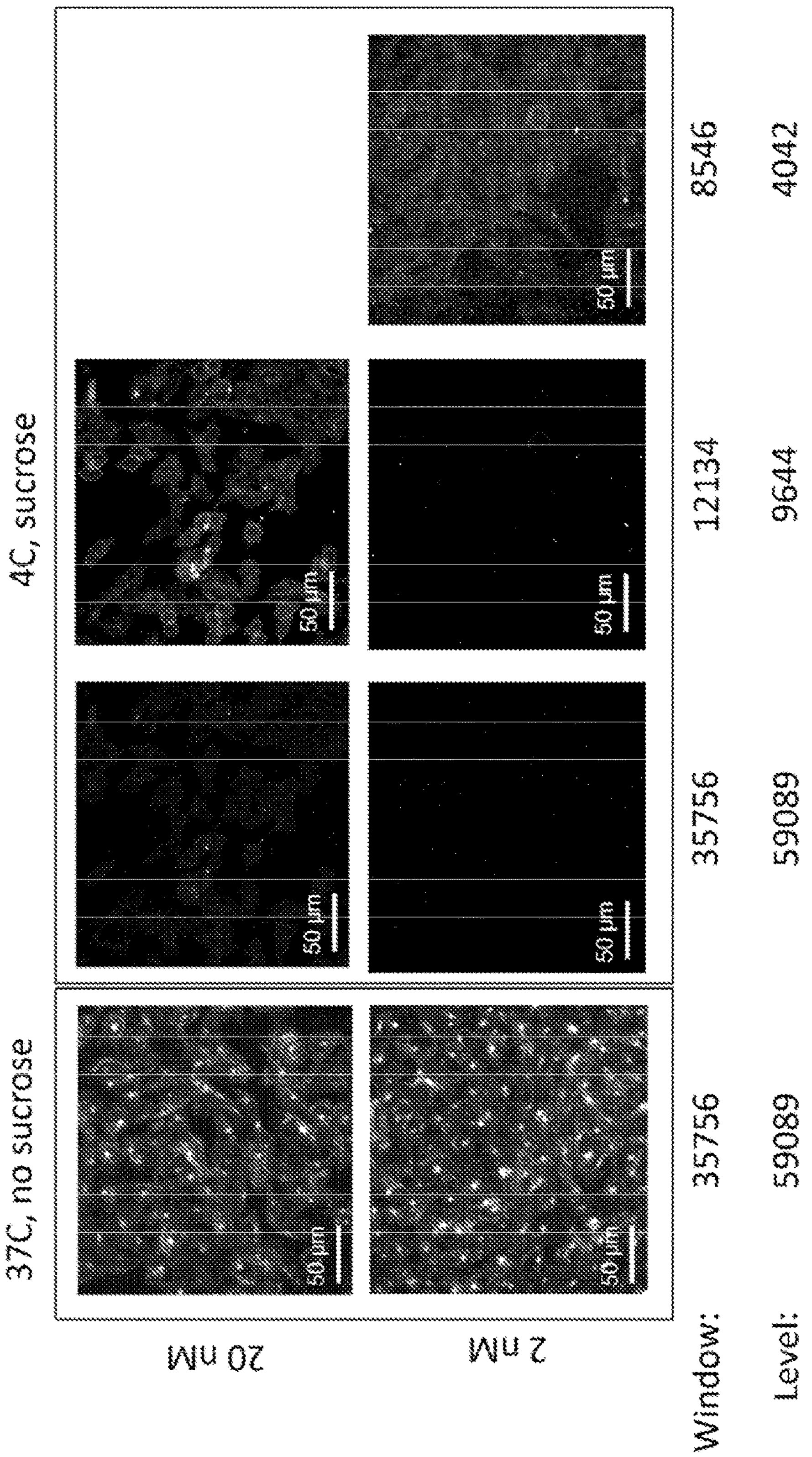
FIG. 2 shows fluorescence micrographs of CHO-K1 cells expressing MOR, taken at 20× for two different concentrations of DRM-800 and with or without sucrose to block internalization. Images are windowed and leveled according to the values specified in the bottom two lines.

The composition and methods described herein demonstrate the use of a fluorescent-labeled agonist to measure expression and internalization of mu opioid receptor, which is useful in many clinical applications.

Opioid use disorder (OUD) can be more effectively managed if immediate, molecular-level in vivo biomarker of a patient's individual pharmacology is available that allows medical-treatment of OUD (MOUD) to be customized. During the past ten years, fluorescence imaging has emerged as a tool to measure receptor concentration in surgical oncology-techniques referred to herein as dynamic multi-agent fluorescence (DMF). Essentially an analog to PET receptor binding methods, DMF method has the added benefit of being low-cost, non-ionizing, portable, and compatible with simultaneous use of multiple fluorescent agents.

In some embodiments, the composition and methods described herein demonstrate the use of a fluorescent-labeled agonist to measure expression and internalization of mu opioid receptor.

In some embodiments, the DMF methods are used to assay mu opioid receptor (MOR) occupancy in vivo using an agent [Lys7]dermorphin-IRDye800CW ("DRM-800"). DRM-800 is a synthetic peptide conjugated to a GMP-available dye, IRDye®800CW. This agent preferentially binds to MORs throughout the body with high affinity and internalization. In some embodiments, DMF measurements can be performed non-invasively in the inner ear of the subject, where the MOR-rich spiral ganglion can be accessed. In some embodiments, the disclosure provides otospectroscopic measurements as a path towards non-invasive in vivo use. This feature is important for the development of a point-of-care device that may one day be used by primary care practitioners to guide therapy.

Medication for treatment of opioid use disorder would greatly benefit from an objective way to optimize dose regimen: Maintenance medications are first-line standard-of-care therapy to prevent relapse and return to illicit drug use in people with OUD. The two most common drugs used in MOUD are methadone, an opioid agonist with a 40 year history, and buprenorphine (Subutex®) a partial MOR agonist, and used either on its own or formulated with naloxone in the form of Suboxone® to prevent diversion and misuse. Naltrexone (Vivitrol®) is an opioid antagonist and works by blocking the effect of opioids, including euphoria. It is recommended as a first-line treatment for mild OUD (Deas et al., 2005; Fishman et al., 2010) to prevent relapse. Naltrexone blocks the effect of opioid agonists and can precipitate withdrawal, whereas methadone and buprenorphine suppress withdrawal symptoms and attenuate the effects of other opioids.

One of the major challenges to treating OUD is that there is no 'one-size-fits-all' approach, and there is currently no evidence to predict which patient will do best with which medication (Bell and Strang, 2019). OUD can be thought of as a chronic condition, requiring a long-term treatment paradigm-those with a more entrenched addiction may require more intensive MOUD and the effect of MOUD and dynamic changes in individual pharmacology may differ depending upon which drug the patient is dependent (Bell and Strang, 2019). The clinical picture is thus one where people often cycle in and out of short terms of MOUD, because of poor response due to variations in treatment delivery, subtherapeutic doses, or pharmacological changes in MOR expression that may, e.g., cause a therapeutic dose to become subtherapeutic due to resensitization of MOR (Zubieta et al., 2000). One of the few human PET binding studies looking at buprenorphine efficacy found that buprenorphine decreases MOR availability (measured as 'binding potential') in a dose-dependent manner, and decreased MOR availability correlates with decreased heroin craving and withdrawal symptoms (Greenwald et al., 2014).

In another embodiment, while there is no evidence to support tapering down doses of MOUD leads to long-term remission (in many people leads to increased likelihood of relapse after treatment discontinuation and risk of overdose after detoxification (Bell and Strang, 2019)), the majority of MOUD patients receiving buprenorphine report a high level of interest in discontinuing the medications (Stein et al., 2019). However, even when buprenorphine discontinuation is planned as a dosing taper, relapse rates are very high, and cycles of leaving and returning to treatment seem to reflect dynamic changes in pharmacological efficacy of MOUD: an objective measurement of receptor occupancy or binding potential changes represents a critical step in providing effective long-term treatment in line with patient-centered shared decision making.

In another embodiment, overdose reversal with naloxone would greatly benefit from an objective way to optimize dose and predict the need for subsequent doses: At least a dozen different natural and synthetic drugs are available and they differ widely in therapeutic range, binding affinity (KD), half-life, and tolerance potential. However, since they exert their effects by modulating MORs, they will enhance analgesia and potentially euphoria, at lower doses, and induce respiratory depression and death at higher ones (Pradhan et al, 2012). Naloxone, a MOR antagonist, competes for receptors when administered during an overdose, effectively acting as an antedote. Overdoses can occur in patients taking high doses of opioids prescribed for pain, such as acute traumatic injury, postsurgical pain, or cancer pain. Overdoses are also common in individuals with OUD following relapse from treatment, when their habitual dose may be more potent than expected due to MOR re-sensitization during the previous period of abstinence.

In another embodiment, synthetic opioids have become more common in abuse, often as an additive to common street drugs like cocaine and heroin. They are approximately 10,000× more potent than morphine and can cause fatal overdose especially in opioid-naïve patients. Even when reversal by naloxone is attempted, because of their potency and their long relative half-life (3-7 hours for carfentanil or fentanyl compared with Naloxone's 60-80 min), fatal overdose can occur after the initial dose of naloxone has worn off. National EMS data from 2015 shows that about 20% of patients receiving naloxone required additional doses (Rzasa Lynn & Galinkin, 2018). However, "overshooting" naloxone dose can lead to ultrarapid opioid detoxification (UROD) and can produce sudden surges in catecholamines with fatal consequences. An objective measurement of MOR availability after initial treatment of naloxone is suspected to have worn off would help determine whether an additional dose of naloxone is required.

An in vivo assay of MOR could drastically impact the management of OUD, given: (1) withdrawal is largely pharmacologically deterministic, in other words, sufficient MOR occupancy by MOUD directly leads to minimizing the cravings associated with illicit drugs, withdrawal symptoms, and risk of relapse; (2) MOUD has a differential effect on individuals with different severity of OUD and who have been exposed to different opioids, in some cases providing therapeutic benefit while in other cases precipitating withdrawal or increasing risk of overdose, and all of which seem to be linked to MOR pharmacology, (3) measurement of MOR occupancy could determine the lowest effective MOUD dose in pregnant women with OUD, but in the absence of this information, higher than needed MOUD doses are given, to the detriment of newborn health, and (4) when overdose is from synthetic opioids, MOR occupancy may help physicians determine whether multiple doses of naloxone are required for reversal.

Over the past decade, new in vivo fluorescence assays have been developed, which are capable of quantifying receptor binding potential, including dual-reporter molecular imaging (Tichauer et al, 2012a), single time point dual-reporter fluorescence imaging (Tichauer et al., 2012b), receptor concentration imaging (Elliott et al., 2016; Samkoe et al., 2014), dual-tracer fluorescence tomography (Davis et al., 2013), ratiometric fluorescence microscopy (Liu et al., 2009), and dual-tracer molecular imaging (Tichauer 2014). For consistency, these methods are referred to generally as dynamic multi-agent fluorescence (DMF) techniques, since they involve measuring or approximating the dynamic kinetic and binding behavior of at least two fluorescent agents to quantify receptor binding, either by acquiring images or collecting optical data using a fiber. The fluorescence approaches are analogous to the PET imaging tools developed for neuropeptide receptor imaging, fitting data directly with compartment models or using Logan graph analysis.

Opioid receptors are located throughout the central nervous system, the peripheral nervous system and widely throughout the body, explaining their diverse role not only in common analgesia and euphoria pathways, but also in respiration, cardiovascular function, thermoregulation, immune function, and gastrointestinal motility (Pradhan et al., 2012). They also mediate several functions in the auditory and vestibular system. The widespread expression of physiologically active receptors explains the many side effects of opioids (e.g., dizziness, nausea, vomiting, respiratory depression, and sudden or rapidly-progressive sensorineural hearing loss (Trescot et al., 2008; Nguyen et al., 2014)).

It is discovered and disclosed here that the inner ear structures are well suited for in vivo MOR measurements because: (i) spiral ganglion neurons (SGNs) are densely populated with MOR receptors, (ii) numerical simulations, previous literature and prior experience suggests NIR excitation light can traverse the tympanum and illuminate the cochlear structures in the vicinity of the round window which are visible otoscopically, and (iii) the extensive clinical reports of profound sensorineural hearing loss following opioid exposure as well as abstinence from heroin suggests an etiology attributed to MOR changes associated with tolerance, resensitization, and hypersensitization.

Embodiments of this disclosure are not limited to the examples presented herein, but are broadly applicable to some other clinical tasks, for example, risk stratification. Moreover, MOR bioavailability before and after initial opioid exposure of a naive patient—for example, a new mother who underwent a cesarean section or a teenager who had wisdom teeth extracted—can be used as a risk biomarker for opioid use disorder in subsequent exposures. In some embodiments, the disclosure provides a point-of-care device as compact as an everyday doctor's otoscope that, following a nasal spray of DRM-800 and IRD-700, can be used to measure MOR binding potential and provide individualized dependency risk assessment (FIG. 1).

As used herein, the term "carrier" refers to a diluent, adjuvant, excipient, or vehicle with which a compound is administered. Non-limiting examples of such pharmaceutical carriers include liquids, such as water and oils, including those of petroleum, animal, vegetable or include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, 21st Edition (University of the Sciences in Philadelphia, ed., Lippincott Williams & Wilkins 2005); and Handbook of Pharmaceutical Excipients, 7th Edition (Raymond Rowe et al., ed., Pharmaceutical Press 2012); each hereby incorporated by reference in its entirety.

As used herein, the term "pharmaceutically acceptable salt(s)" includes salts of acidic or basic groups which may be present in a compound. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts. Particularly preferred salts include phosphate and gluconate salts.

The following items form part of this disclosure:

Item 1: A compound of formula (I) or a salt thereof:

(I)

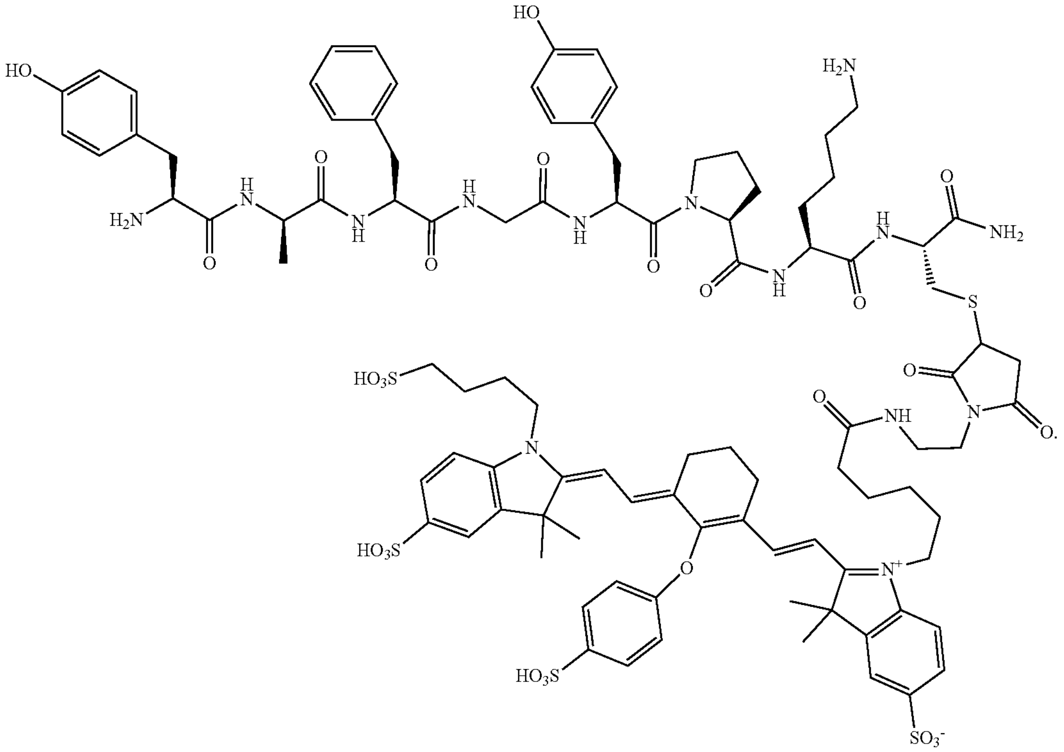

Item 2: A composition comprising the compound of Item 1 and a carrier.

Item 3: A method for determining occupancy level of an opioid receptor in a subject, comprising:

(a) contacting at least one probe with the subject, wherein the probe binds specifically to the opioid receptor (OR);

(b) measuring intensity of fluorescent signal emitted by the probe from inner ear of the subject; and (c) determining the occupancy level of the opioid receptor in the subject based on the fluorescence intensity.

Item 4: The method of Item 3, wherein the probe comprises a compound having the formula (I) or a salt thereof:

(I)

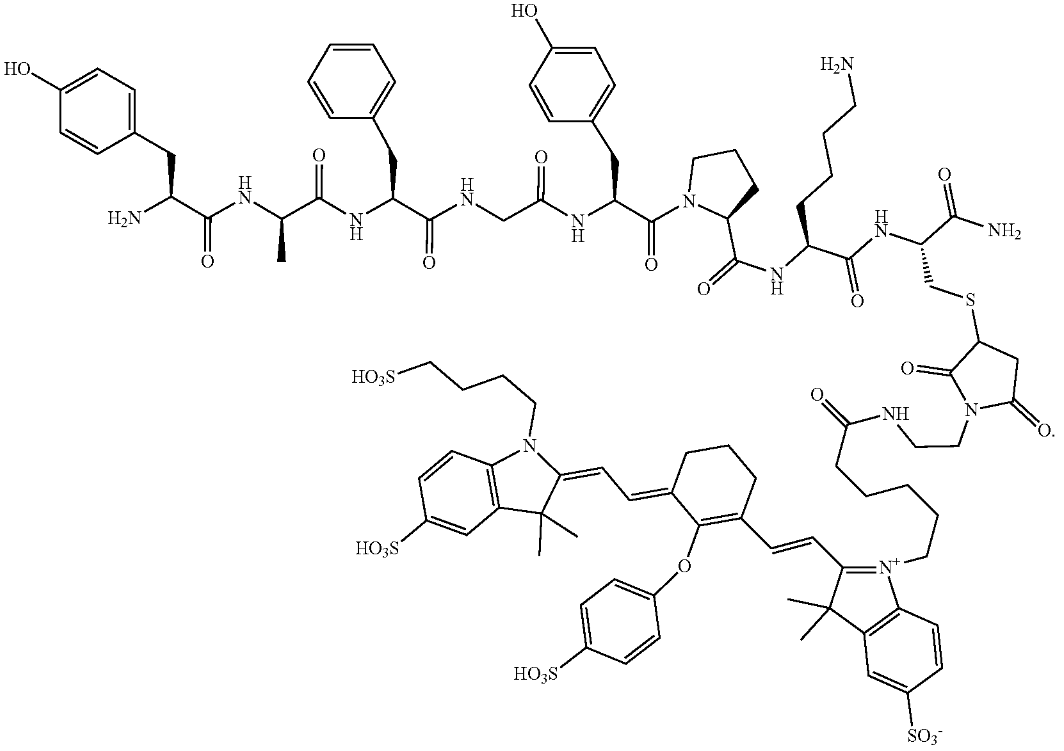

Item 5: The method of any one of Items 3 and 4, wherein step (b) is performed non-invasively.

Item 6: The method of any one of Items 3-5, wherein fluorescence intensity in spiral ganglion is measured in step (b).

Item 7: The method of any one of Items 3-6, wherein the fluorescence intensity is measured by using an oto-spectroscope.

Item 8: The method of any one of Items 3-7, wherein the opioid receptor is mu opioid receptor (MOR).

Item 9: The method of any one of Items 3-8, wherein the occupancy level of the opioid receptor in the subject is calculated quantitatively.

Item 10: The method of any one of Items 3-9, wherein higher fluorescence intensity indicates lower occupancy level of the opioid receptor.

Item 11: The method of any one of Items 3-10, further comprising administering an effective amount of an opioid antagonist or a partial opioid agonist to the subject based on the occupancy level of the opioid receptor in the subject.

Item 12: The method of any one of Items 3-11, wherein the amount of the opioid antagonist or the partial opioid agonist administered is determined based on the occupancy level of the opioid receptor in the subject.

Item 13: The method of any one of Items 3-12, wherein the probe is administered into the body of the subject in step (a).

Item 14: The method of any one of Items 3-13, wherein the probe is administered by a means selected from the group consisting of nasal spray, intravenous (IV) injection, oral administration and skin patch.

Item 15: The method of any one of Items 3-14, wherein the subject has been treated with a pain medication prescribed by a physician prior to step (a).

Item 16: The method of any one of Items 3-15, wherein the method is used for preventing/treating opioid use disorder (OUD) or for monitoring response of a subject to treatment using an opioid antagonist.

Item 17: The method of any one of Items 3-15, wherein the method is used for determining the dose of pharmacotherapy in the treatment of substance use disorder.

Item 18: The method of Item 17, wherein the substance use disorder is opioid use disorder.

Item 19: The method of any one of Items 3-15, wherein the method is used to taper down the dosage of pharmacotherapy.

Item 20: The method of any one of Items 3-19, wherein the subject is a pregnant woman with a substance use disorder and the method is used to reduce the risk of relapse in the subject.

Item 21: The method of any one of Items 3-20, wherein excitation wavelength used in step (b) ranges between 635 nm and 760 nm Item 22: The method of any one of Items 3-21, further comprising a step of measuring rate of internalization of the probe.

Item 23: The method of any one of Items 3-22, wherein two or more probes are used simultaneously.

Item 24: The method of any one of Items 3-23, wherein the occupancy level of the opioid receptor and the rate of internalization of the probe are used to evaluate risk of developing an opioid use disorder in the subject.

Item 25: The method of any one of Items 3-24, wherein the method is performed at point-of-care.

Item 26: The method any one of Items 3-25, wherein an opioid antagonist is administered, and the opioid antagonist is selected from the group consisting of alvimopan, norbinaltorphimine, nalmefene, naloxone, naltrexone, methylnaltrexone, and nalorphine, and pharmaceutically acceptable salts or prodrugs thereof.

Item 27. A kit for detecting an opioid receptor in a subject, comprising (a) a predetermined amount of compound of formula (I); and (I)

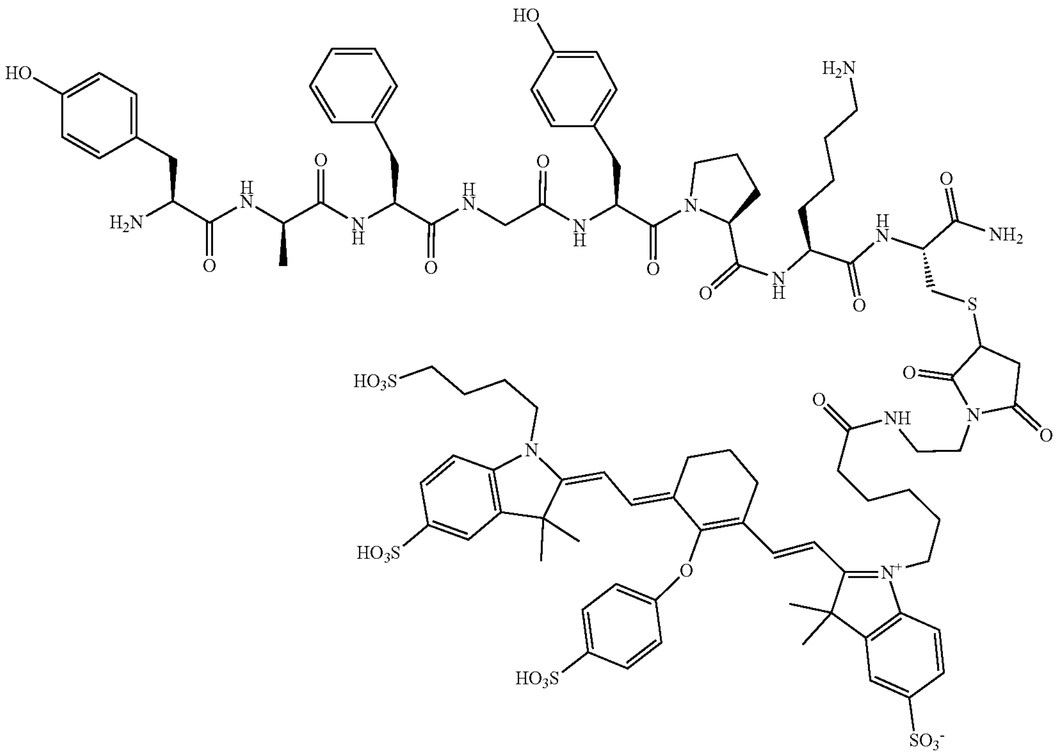

(b) instruction for using the kit.

EXAMPLES

Example 1: Preparation Method for Fluorescent-Labeled Opioid Agonist DRM-800

Preparation of the unlabeled peptide was performed using standard Fmoc-based solid-phase peptide synthesis (SPPS) methods as follows: Rink Amide AM resin (0.141 g, 0.1 mmol, 0.71 mmol/g loading) was swollen in DMF for 30 min, then drained. This was followed by initial Fmoc deprotection (20% piperidine/DMF, shaken for 1 min; drained; washed with DMF; repeated once). After DMF wash (shaken for 15 sec; drained; repeated twice), sequential coupling of the remaining residues began. This involved adding the appropriate Fmoc amino acid (0.5 mmol) pre-combined with HCTU (0.5 mmol) in DMF (1.5 mL) to the resin. After mixing for 20 seconds, DIEA (0.17 mL, 1 mmol) was added and the mixture was shaken for 3 min. After DMF wash (shaken for 15 sec; drained, repeated twice) the previous piperidine deprotection conditions were used. These steps were repeated for each added amino acid. After final Fmoc deprotection, the resin was sequentially washed with DMF and DCM (twice each). Peptide removal from the resin with global deprotection was accomplished with the addition of resin cleavage solution (5× resin volume, TFA/triisopropylsilane/thioanisole/anisole, volume ratio 92:4:2:2) and shaking for 1 h at r.t. The TFA solution was collected, mixed with cold diethyl ether, and the precipitated crude YdAFGYPKC-$NH_2$ was separated by centrifugation, dissolved in water and lyophilized. LCMS of the crude peptide LCMS (Phenomenex Kinetex 2.6u XB-C18 100A column, 100×2.10 mm; acetonitrile gradient 0 to 70% in $H_2O$-formic acid (0.1%) in 15 min, flow rate 0.2 mL/min): retention time 9.0 min, m/z calculated 947, found 474 ($M+2H^+$), 948 ($M+H^+$); 946 ($M-H^+$).

Labeling with IRDye 800CW [based on Bioorg. Med. Chem. Lett. 2011, 21, 1146-1150]: to a solution of the crude YdAFGYPKC-$NH_2$ (10 mg) in PBS buffer (pH 7.2-7.4, 10 mL) was added IR Dye 800CW (18 mg), and the mixture was incubated for 2.5 h at r.t. The resulting solution was diluted with 20 mL of 0.1% TFA in water and purified by HPLC (Phenomenex Jupiter Proteo 4u AXIA 90A column, 250×21.20 mm; methanol gradient 50 to 100% in $H_2O$-TFA (0.1%) in 20 min, flow rate 15 mL/min, collecting the fractions eluting between 9 and 13 min). The product-containing fractions were combined and lyophilized to afford 2 mg of IRDye 800CW-labelled YdAFGYPKC-$NH_2$. LCMS (Phenomenex Kinetex 2.6u XB-C18 100A column, 100×2.10 mm; acetonitrile gradient 0 to 70% in $H_2O$-formic acid (0.1%) in 15 min, flow rate 0.2 mL/min): retention time 12.5 min, m/z calculated 2072, found 1035 ($M-2H^+$).

The chemical structure of DRM-800, [Lys7]Dermorphin (YAFGYPK-$NH_2$), with cystine added and conjugated to maleimide-functionalized IRDye800CW is as shown in Formula I.

Formula (I)

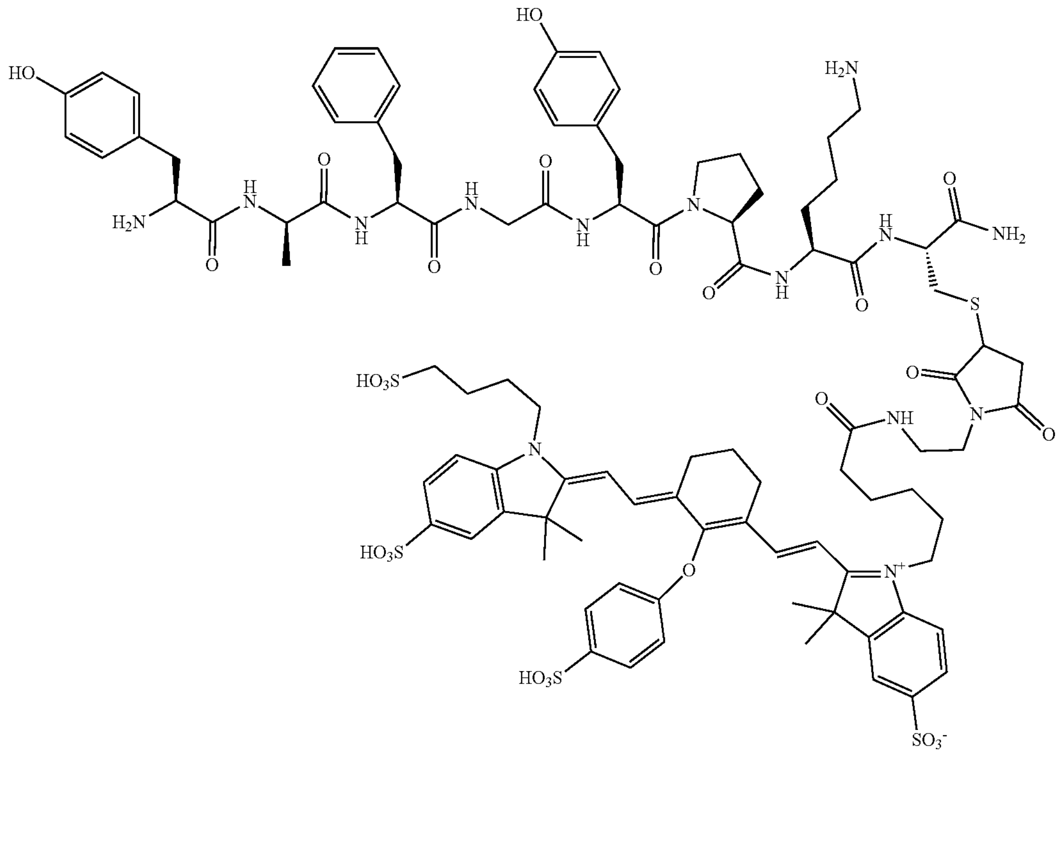

Electrospray ionization (ESI) analysis was performed to show the ions detected and liquid chromatography readout was used to isolate the conjugate, with parameters shown below:

Peptide Sequence: YAFGYPKC (SEQ ID NO:1)
Molecular weight 1051 g/mol
Extinction coefficient 2800 cm−1 M−1

Example 2: Fluorescence-Labeled Opioid Agonist DRM-800 Binds to Mu-Opioid Receptor (MOR) and is Rapidly Internalized in Vitro To determine the binding kinetics of DRM-800 in vitro, a competitive assay was performed by simultaneously incubating Chinese hamster ovarian (CHO-K1) host cells expressing human mu-opioid receptor (ES-542-C OP3 ValiScreen, PerkinElmer) with 50 nM of DRM-800 and concentrations of MOR antagonist, naloxone, ranging from 100 μM to 5 μM. Cells were washed with PBS twice, and then imaged on the LI-COR Oddysey. Specific binding of DRM-800 was calculated from the percent fluorescence signal compared to controls (DRM-800 with no naloxone, and no naloxone or DRM-800).

Figure 3:
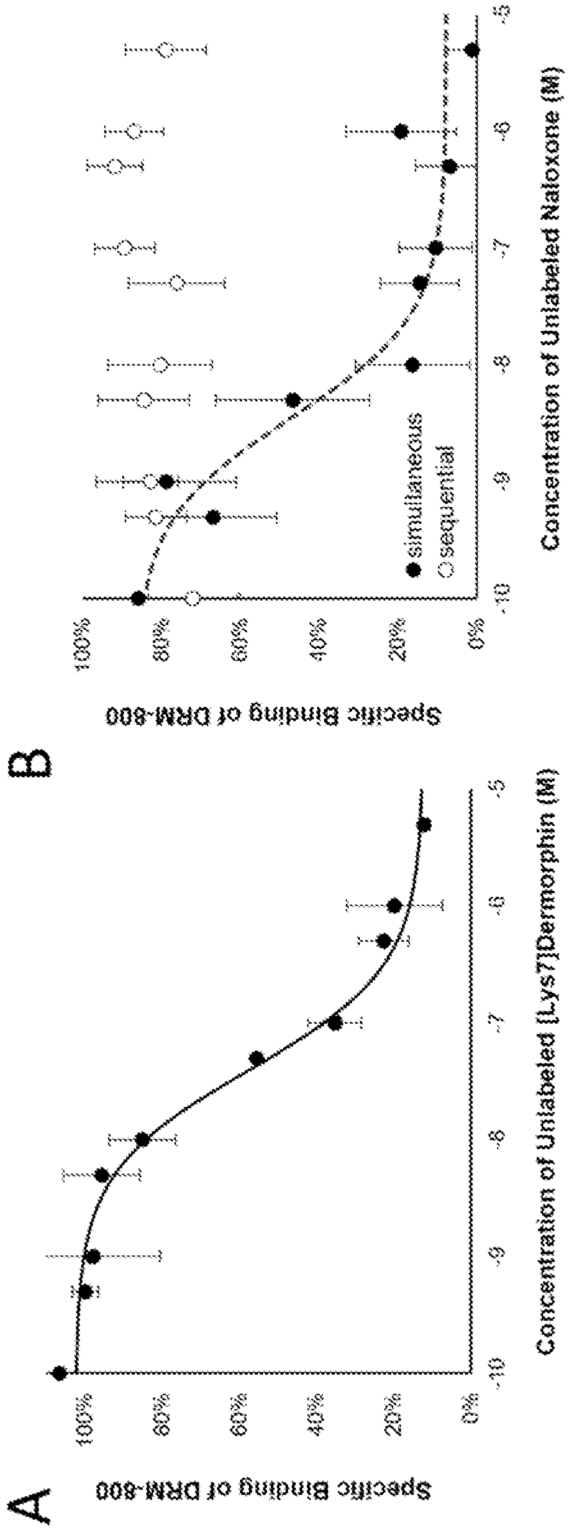
FIG. 3 shows results of two competitive binding assays. (A) Cells were incubated with 2 nM concentrations of DRM-800 and simultaneously with [Lys7]Dermorphin across a range of concentrations. (B) Cells were either simultaneously (black circles) incubated with DRM-800 at 50 nM and a range of naloxone concentrations, or they were sequentially (open circles) incubated with DRM-800 being administered 30 minutes before naloxone for another 30 minutes.

FIG. 3 shows results of two competitive binding assays. (A) Cells were incubated with 2 nM concentrations of DRM-800 and simultaneously with [Lys7]Dermorphin across a range of concentrations. (B) Cells were either simultaneously incubated with DRM-800 at 50 nM and a range of naloxone concentrations, or they were sequentially incubated with DRM-800 being administered 30 minutes before naloxone for another 30 minutes.

The IC50 was determined to be 3.5 nM by fitting the data with a one-site competitive binding nonlinear regression model (Prism 8.2.1, Graphpad Software, Inc., San Diego, CA). Using an assumed kD for naloxone obtained from literature (Kd=11.3 nM, Newman L C et al, 2000) the Ki for DRM-800 was determined to be 0.64 nM, which represents a fairly high affinity for OPRM1.

When the same experiment was performed in a slightly different manner, i.e., rather than adding DRM-800 and naloxone simultaneously, the agents were added sequentially with naloxone being added 10 min after DRM-800, very different kinetics were observed. In this case, the retained DRM-800 after washing was similar to the across all concentrations (open circles), suggesting that the DRM-800 bound to MOR are quickly internalized and therefore cannot be displaced even at high concentrations of naloxone, which does not enter the cell.

Example 3: Plasma Pharmacokinetics were Obtained Following Intravenous Administration of DRM-800

Figure 4:
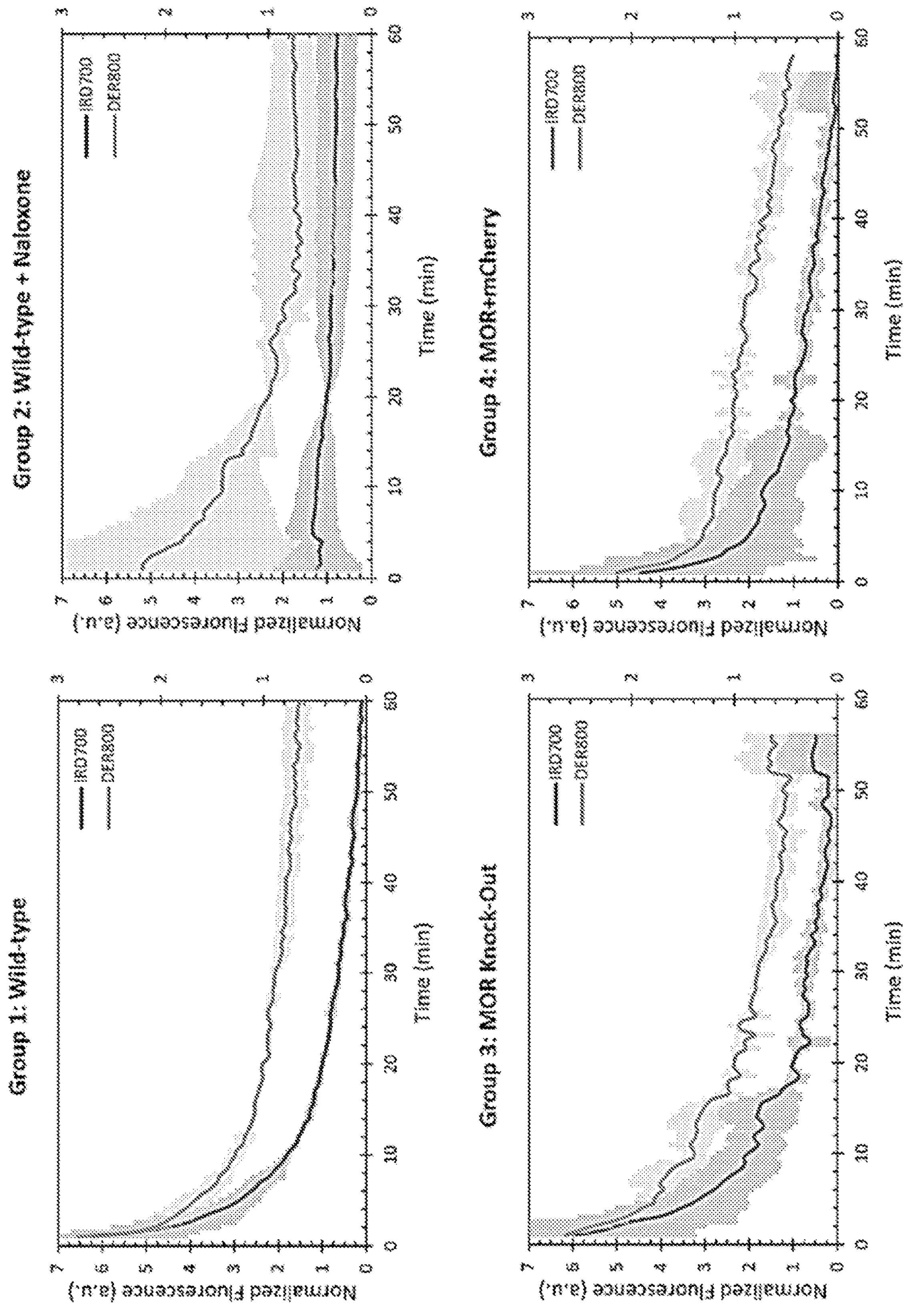
FIG. 4 shows plasma curves for IRD700 and DRM800 in (A) wildtype, (B) Naloxone-blocked, (C) MOR-knockout mice, and (D) MOR+mCherry knockin mice.
Figure 5:
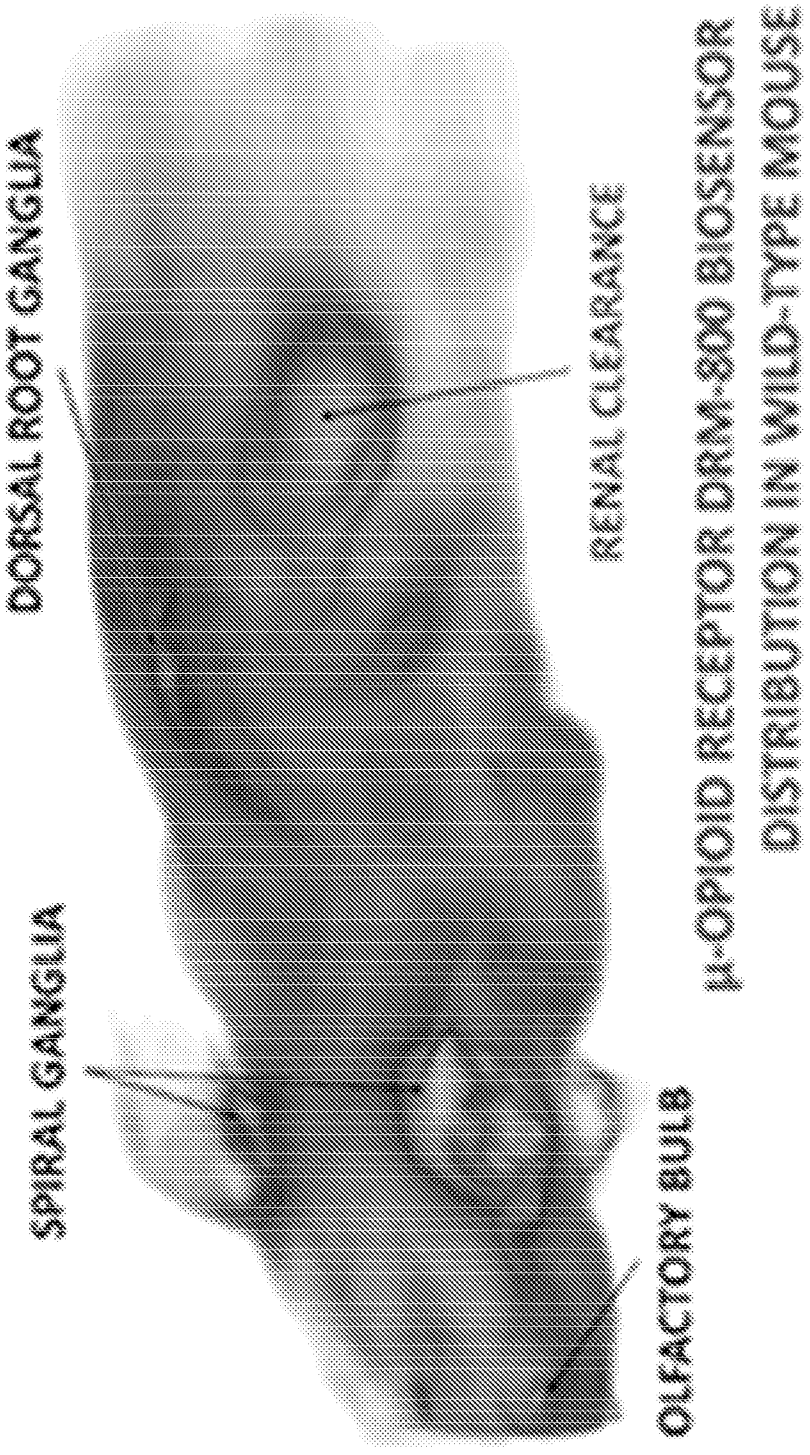
FIG. 5 shows whole-body distribution of 3 nmoles of DRM-800, a fluorescent MOR agonist, 60 minutes after injection, imaged using BioSlicer imaging macrocryotome. MOR-rich structures are highlighted.

Following in vitro characterization, DRM-800 plasma curves were obtained using a previously described method of direct carotid artery imaging (Elliott J T et al., 2014). DRM-800 and IRDye700CX were coinjected into mice and imaged using the LI-COR Pearl. Intravenous injection of DRM-800 is well-tolerated by mice and remains in plasma for at least one hour. The plasma half-life (time in which the concentration of dye is 50% of initial) for DRM-800 was 7.95 min and 12.6 min for wildtype and knockout mice, respectively. However, the biexponential half-lives (half-lives for each compartment) were also calculated. The distribution (a) and elimination (β) half-lives were 3.3 (3.1-3.5) min and 70.8 (67.2-74.8) min, respectively, for wildtype mice and 6.2 (4.9-8.6) min and 45 (33-68) min, respectively, for knockout mice. FIG. 4 shows the mean plasma curves for DRM-800 and IRDye700DX for each group of mice.

Example 4: Intensity of Fluorescence Following Administration of DRM-800 is Associated with MOR Expression in Particular Anatomical Locations DRM-800 and IRDye700CX were administered in wild-type and MOR knock out mice, and 1 hour later the animals were sacrificed, frozen and prepared for ex vivo imaging. An imaging cyromacrotome was used to image the mice whole-body every 150 um using a fluorescence multispectral approach. Multispectral images were acquired during white light and during 635 nm excitation and additionally, fluorescence emission was acquired during 760 nm excitation. In this way, white-light color images, as well as unmixed fluorescence from IRDye700 and DRM-800 were determined for each slice, and the slices were combined for 3D rendering of the fluorescence distribution.

The intensity of DRM-800 in structures identified as the spiral ganglion and dorsal root ganglion were compared with intensity of IRDye700CX (untargeted blood flow marker). These results were compared between wildtype and MOR-knockout mice to determine whether enhancement found in the ganglia were specific to MOR expression. The results of this analysis were compelling. The average fluorescence intensity in the wildtype mice for spiral ganglion ROIs were 7810±610 RFUs compared with 2894±729 RFUs in the MOR knockout mice. For the dorsal root ganglion ROIs, which were selected as the region around the spinal processes, the mean intensity was 4356±253 RFUs and 2089±85 RFUs for the wildtype and knockout mice, respectively. These results demonstrate mu opioid receptor-specific enhancement by DRM-800 in the structures of interest 1 hour post-injection.

Figure 6A:
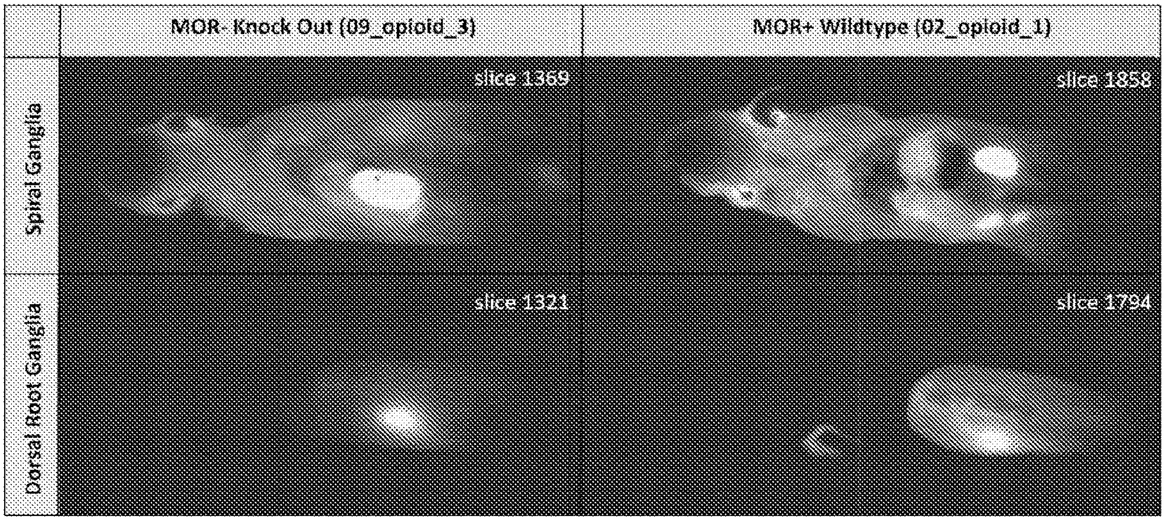
FIG. 6A shows DRM-800 channel fluorescence 1 hour after injection in wild type (right) and MOR knockout (left) mice, showing the enhancement of the spiral ganglion and dorsal root ganglion is dependent on the presence of MOR.
Figure 6B:
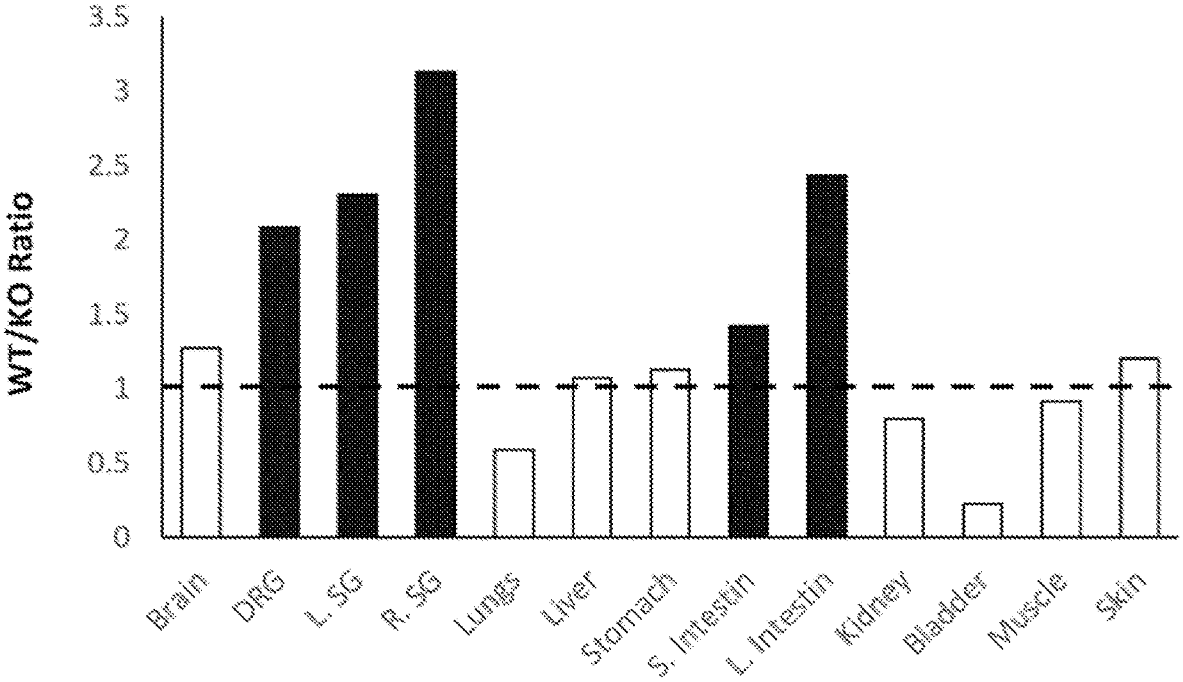
FIG. 6B shows the ratio of fluorescence intensity RFU values obtained with ROI analysis in the wildtype (WT) and knockout (KO) mice. Structures with a ratio>1 are coded as black bars (n=2).

FIG. 6B shows the ratio of enhancement in the wildtype mouse compared to that in the knockout mouse. The right spiral ganglion showed the largest difference in enhancement, with an intensity of 3.1× that of the knockout mouse. The left spiral ganglion, dorsal root ganglia and intestines showed higher enhancement in the wildtype mice compared to knockout mice, all of which are regions known to have higher expression levels of MOR.

Example 5: Kinetic Model of Internalized Dye Sensitive to Receptor Concentration and Rate of Internalization Graphical analysis (e.g., LOGAN or PATLAK methods in PET imaging) provide a quick way to calculate the accumulation or binding potential of tissue over time, reported as the slope. The uptake of FDG in pathological cancer cells is different than the internalization of opioid agonist in normal cells, however, the process can be modeled in a similar way for molecules that are rapidly internalized. The increase in signal over time will be due to both the availability of MORs and the rate of internalization. In some embodiments, the disclosure provides a kinetic model that describes the measured signal changes and derived 'opioid SUV' or OSUV over time, based on different concentrations of receptors, available receptors and internalization rates. Signal changes are also shown for IRDye700CW and fluorescein naloxone, which could act as a third tracer for more complex models.

Figure 7A:
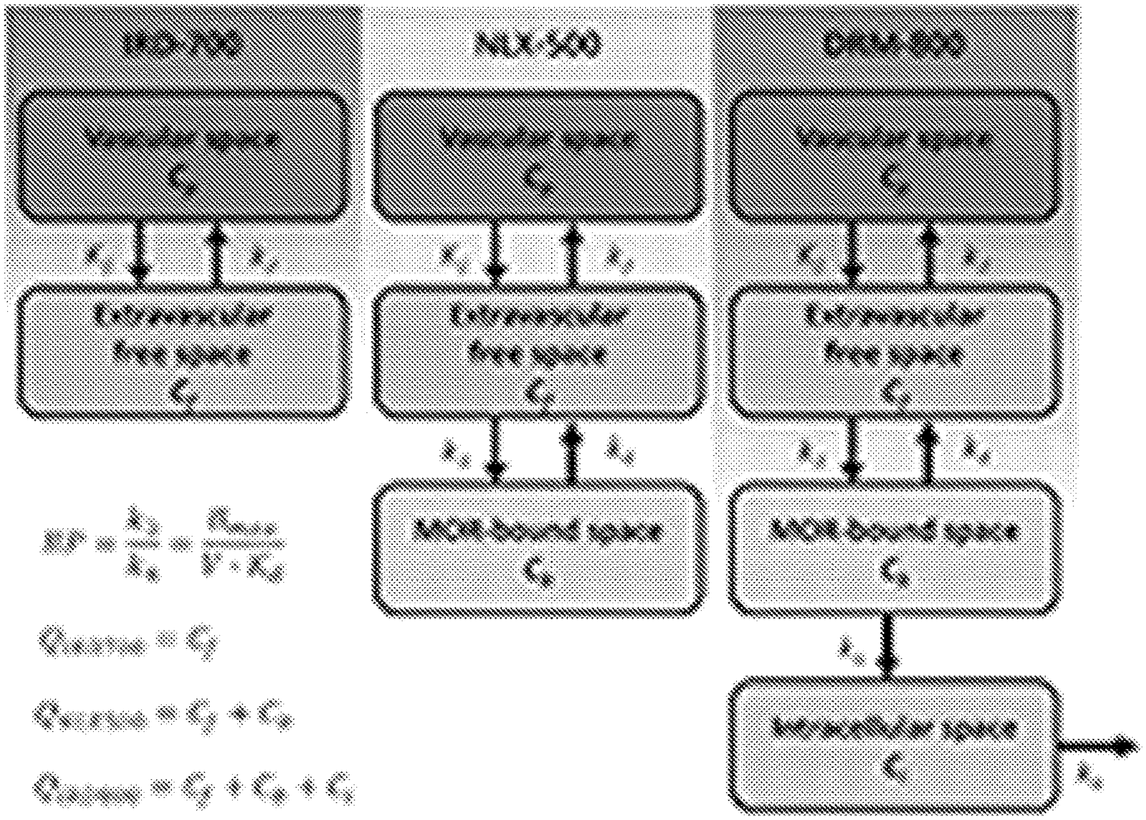
FIG. 7A shows compartment models (two-, three- and four-) represent the distribution volumes of IRD-700, NLX-500, and DRM-800.
Figure 7B:
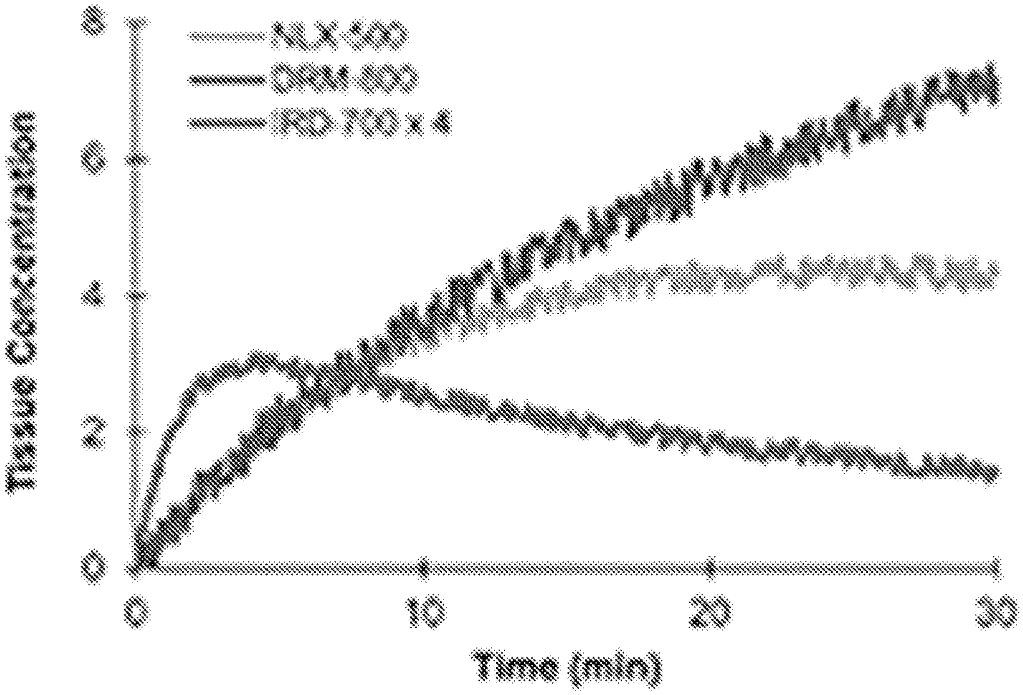
FIG. 7B shows tissue uptake curves.
Figure 7C:
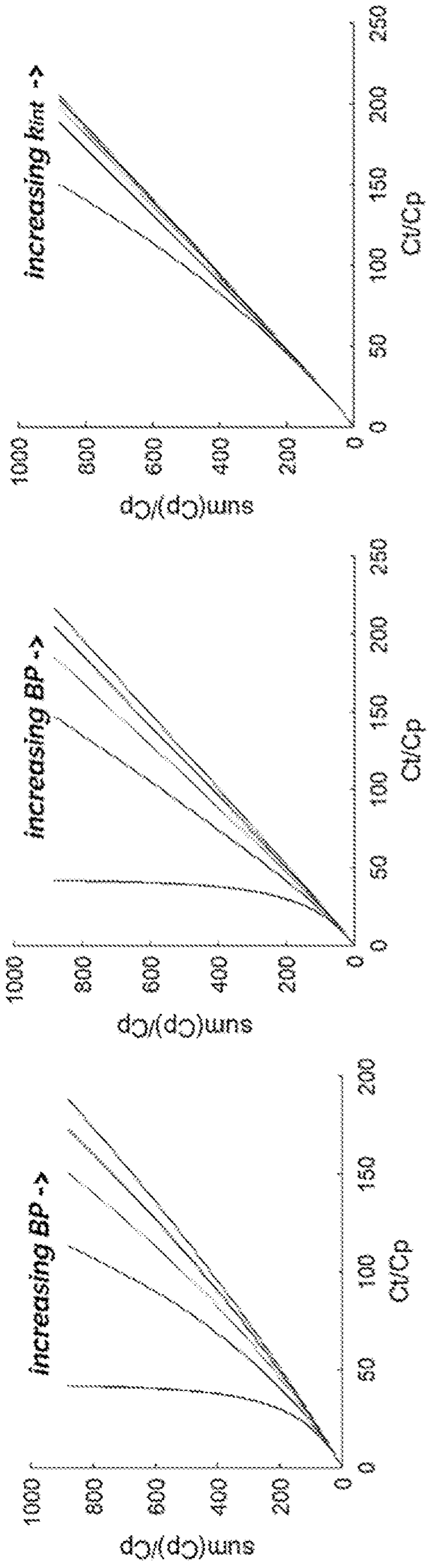
FIG. 7C shows graphical analysis plots for increasing BP with internalization (left) and without internalization (middle), and for the same BP with increasing internalization.
Figure 8:
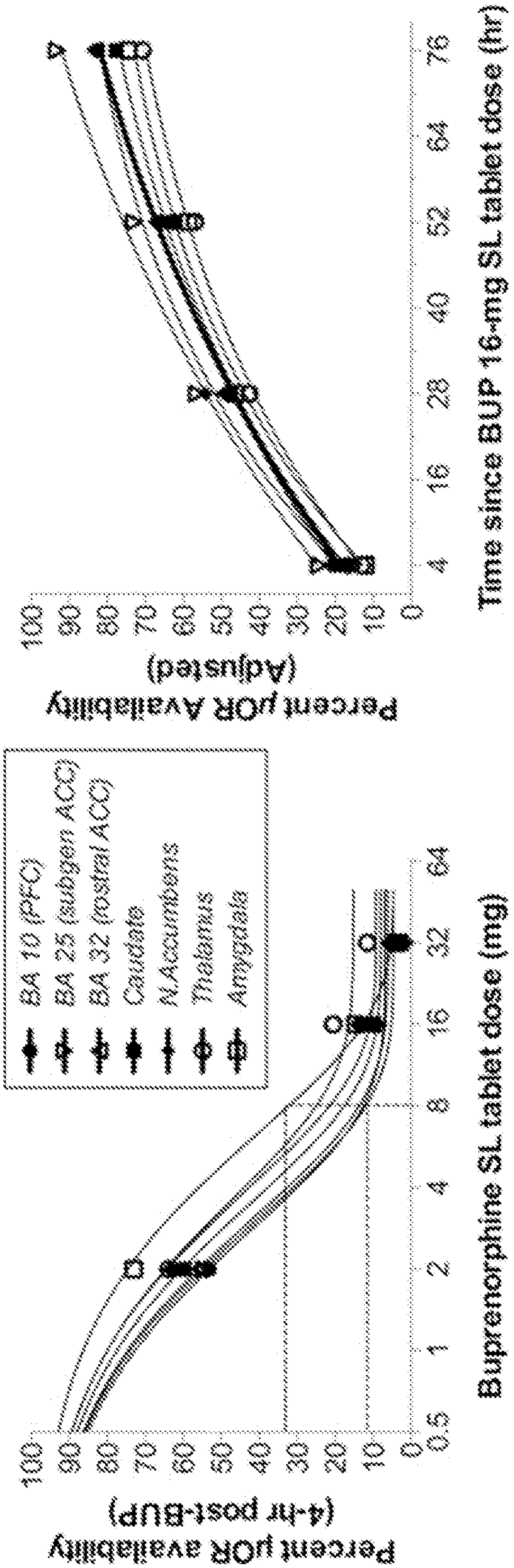
FIG. 8 shows relationship between MOR availability and buprenorphine dose (Zubieta et al., 2000; Greenwald et al., 2006).

Compartment modeling was used to describe the transfer of mass of DRM-800 between compartments. A three-tissue compartment model was used to describe the time-dependent distribution of DRM-800 in the vascular, extravascular free, bound and intracellular spaces. FIG. 7 summarizes the compartment model used in the numerical simulations, which were performed for theoretical tissue structure of interest of a volume of 123 $mm^3$ and containing about 42,000 ganglion neurons, which is consistent with a structure like the spiral ganglion. rate constants used in the simulation were $K_1$=0.3 min-1, $k_2$=0.01 min-1, $k_4$=0.04 min-1, and $k_5$=0.01 min-1, and $k_3$=BPND×$k_4$. Binding potential (BP) was estimated, based on the Bmax and Kd inferred from in vitro assays, to be approximately 10. The relationship between buprenorphine dose and binding potential (FIG. 7B) was modeled after reported MOR occupancy rates measured by PET imaging (15). FIG. 7C shows the tissue fluorescence curves for DRM-800 and, for purposes of comparison, two other fluorophores: fluorescein-labeled naloxone (NLX-500) that binds but does not internalize, and IRDye®700DX (IRD-700) that does not bind. The binding potential of DRM-800 in this case is 9.0.

Figure 9C:
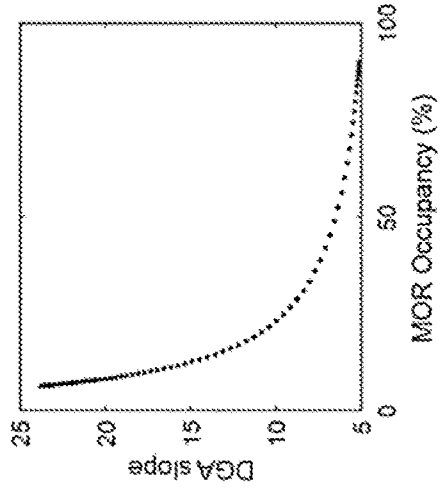
FIG. 9A-9C shows simulated data using the model of FIG. 8, showing the different Graphical Analysis plots for different doses of Buprenorphine, and the relationship between dose and slope of the DGA.
Figure 9B:
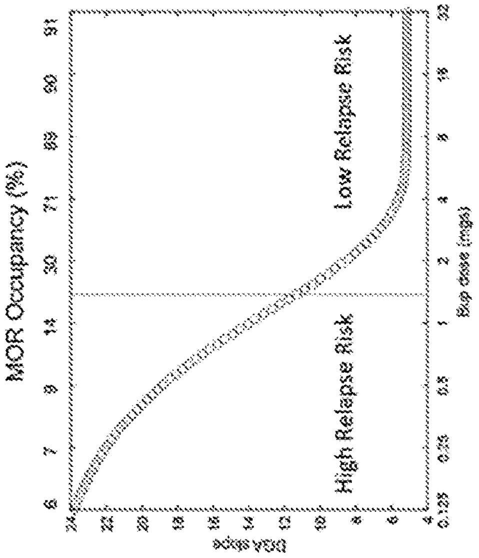
Figure 9A:
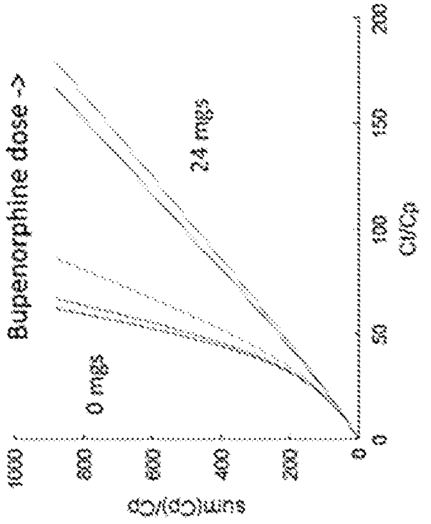

Example 6: Application of Kinetic Model to Evaluate Receptor Occupancy for Establishing Medical Assisted Treatment (MAT), Dose Tapering Down, and Efficacy of Antagonist A dose-dependent increase in MOR occupancy is observed with increasing buprenorphine dose. Total withdrawal symptoms and heroin craving scores were correlated with MOR availability, and therefore one embodiment of this invention is to use a surrogate of MOR occupancy, nondisplaceable binding potential (BPND) which is proportional to the DRM-800 graphical analysis (DGA) slope. Numerical experiments were performed by using the following model for percent MOR availability as a function of bupenorphine tablet dose (MK Greenwald et al., 2015). NB: MOR occupancy (%) is one hundred minus MOR availability (%). Assuming that in the absence of MOR occupancy, the BPND of MOR in the ganglia and other structures of interest is approximately 4.0, the DGA plot was simulated for occupancies associated with bupenorphone doses from 0 mg to 32 mg. FIG. 9B shows the relationship between DGA and bupenorphine dose or MOR occupancy (%). FIG. 9C shows a slightly different way of looking at the data, where DGA slope maps directly to MOR occupancy, and could be used to titrate appropriate dose.

Clinicians need to be aware of individual differences in buprenorphine plasma pharmacokinetics when prescribing maintenance doses to ensure low MOR availability, because MOR availability is correlated with withdrawal symptoms and heroine craving—predictors of relapse or suicide.

This result is consistent with a clinical heuristic that opioid blockade (more so than withdrawal suppression) should be the primary criterion guiding BUP maintenance dose, especially during phases of treatment when a patient is using opioids in the absence of withdrawal (e.g., early recovery).

A clinician could therefore titrate BUP maintenance dose to DGA slope, which would be independent of differences in metabolism or clearance of BUP, instead of subjective measures.

In pregnant women who are undergoing MOUD, there is a trade-off when considering dose of methadone or buprenorphine: high doses of replacement opioids can still have negative effects on fetal growth, risk of gastroschisis, preterm birth and neonatal abstinence syndrome (NAS); however, it is widely agreed that MOUD is strongly preferable to untreated addiction with relapse and withdrawal cycles that expose a fetus to dramatically changing levels of plasma opioids, creating repeating bouts of physiological withdrawal. In one embodiment, this disclosure would provide an objective, precise way to dose each individual, avoiding the risk of relapse and illicit drug use, while minimizing deleterious effects to the fetus as much as possible.

REFERENCES

The following references cited in this disclosure are incorporated herein in their entirety:

Bell J, Strang J. Medication Treatment of Opioid Use Disorder. Biological psychiatry. 2019 Jul. 2.

Belzeaux R, Lalanne L, Kieffer B L, Lutz P E. Focusing on the opioid system for addiction biomarker discovery. Trends in molecular medicine. 2018 Feb. 1; 24(2):206-20.

Carr J A, Valdez T A, Bruns O T, Bawendi M G. Using the shortwave infrared to image middle ear pathologies. *Proc Natl Acad Sci* USA. 2016 Sep. 6; 113(36):9989-94. doi: 10.1073/pnas.1610529113. Epub 2016 Aug. 22. PMID: 27551085; PMCID: PMC5018751.

Christenson B J, Matjala A R. Two cases of sudden sensorineural hearing loss after methadone overdose. Annals of Pharmacotherapy. 2010 January; 44(1):207-10.

Davis S C, Samkoe K S, Tichauer K M, Sexton K J, Gunn J R, Deharvengt S J, Hasan T, Pogue B W. Dynamic dual-tracer MRI-guided fluorescence tomography to quantify receptor density in vivo. Proceedings of the National Academy of Sciences. 2013 May 28; 110(22): 9025-30.

Deas D, May M K, Randall C, Johnson N, Anton R. Naltrexone treatment of adolescent alcoholics: an open-label pilot study. Journal of Child & Adolescent Psychopharmacology. 2005 Nov. 1; 15(5):723-8.

Elliott J T, Tichauer K M, Samkoe K S, Gunn J R, Sexton K J, Pogue B W. Direct characterization of arterial input functions by fluorescence imaging of exposed carotid artery to facilitate kinetic analysis. Molecular Imaging and Biology. 2014 Aug. 1; 16(4):488-94.

Elliott J T, Samkoe K S, Davis S C, Gunn J R, Paulsen K D, Roberts D W, Pogue B W. Image-derived arterial input function for quantitative fluorescence imaging of receptor-drug binding in vivo. Journal of biophotonics. 2016 March; 9(3):282-95.

Elliott J T, Dsouza A V, Marra K, Pogue B W, Roberts D W, Paulsen K D. Microdose fluorescence imaging of ABY-029 on an operating microscope adapted by custom illumination and imaging modules. Biomedical optics express. 2016 Sep. 1; 7(9):3280-8.

Elliott J T, Marra K, Evans L T, Davis S C, Samkoe K S, Feldwisch J, Paulsen K D, Roberts D W, Pogue B W. Simultaneous in vivo fluorescent markers for perfusion, protoporphyrin metabolism, and EGFR expression for optically guided identification of orthotopic glioma. Clinical Cancer Research. 2017 May 1; 23(9):2203-12.

Fishman M J, Winstanley E L, Curran E, Garrett S, Subramaniam G. Treatment of opioid dependence in adolescents and young adults with extended release naltrexone: Preliminary case-series and feasibility. Addiction. 2010 September; 105(9):1669-76.

Freeman S R, Bray M E, Amos C S, Gibson W P. The association of codeine, macrocytosis and bilateral sudden or rapidly progressive profound sensorineural deafness. Acta oto-laryngologica. 2009 Jan. 1; 129(10):1061-6.

Frost J J, Douglass K H, Mayberg H S, Dannals R F, Links J M, Wilson A A, Ravert H T, Crozier W C, Wagner Jr H N. Multicompartmental analysis of [11C]-carfentanil binding to opiate receptors in humans measured by positron emission tomography. Journal of Cerebral Blood Flow & Metabolism. 1989 June; 9(3):398-409.

Greenwald M K, Comer S D, Fiellin D A. Buprenorphine maintenance and mu-opioid receptor availability in the treatment of opioid use disorder: implications for clinical use and policy. *Drug Alcohol Depend.* 2014 Nov. 1; 144:1-11. doi: 10.1016/j.drugalcdep.2014.07.035. Epub 2014 Aug. 19. PMID: 25179217; PMCID: PMC4252738.

Greenwald M K, Johanson C E, Moody D E, Woods J H, Kilbourn M R, Koeppe R A, Schuster C R, Zubieta J K. Effects of buprenorphine maintenance dose on μ-opioid receptor availability, plasma concentrations, and antagonist blockade in heroin-dependent volunteers. Neuropsychopharmacology. 2003 November; 28(11):2000.

Harell M, Shea J J, Emmett J R. Total deafness with chronic propoxyphene abuse. The Laryngoscope. 1978 September; 88(9):1518-21.

Ho T. Hydrocodone use and sensorineural hearing loss. Pain Physician. 2007 May; 10:467-72.

Iqbal N. Recoverable hearing loss with amphetamines and other drugs. Journal of psychoactive drugs. 2004 Jun. 1; 36(2):285-8.

Ishiyama A, Ishiyama G, Baloh R, Evans C. Heroin-induced reversible profound deafness and vestibular dysfunction. Addiction. 2001 Sep. 1; 96(9):1363-4.

Johansson J, Hirvonen J, Lovra Z, Ekblad L, Kaasinen V, Rajasilta O, Helin S, Tuisku J, Siren S, Pennanen M, Agrawal A. Intranasal naloxone rapidly occupies brain mu-opioid receptors in human subjects. Neuropsychopharmacology: official publication of the American College of Neuropsychopharmacology. 2019 Mar. 13.

Lammertsma A A, Hume S P. Simplified reference tissue model for PET receptor studies. Neuroimage. 1996 Dec. 1; 4(3):153-8.

Liu J T, Helms M W, Mandella M J, Crawford J M, Kino G S, Contag C H. Quantifying cell-surface biomarker expression in thick tissues with ratiometric three-dimensional microscopy. Biophysical journal. 2009 Mar. 18; 96(6):2405-14.

Logan J, Fowler J S, Volkow N D, Wang G J, Ding Y S, Alexoff D L. Distribution volume ratios without blood sampling from graphical analysis of PET data. Journal of Cerebral Blood Flow & Metabolism. 1996 September; 16(5):834-40.

Mintun M A, Raichle M E, Kilbourn M R, Wooten G F, Welch M J. A quantitative model for the in vivo assessment of drug binding sites with positron emission tomography. Annals of Neurology: Official Journal of the American Neurological Association and the Child Neurology Society. 1984 March; 15(3):217-27.

Newman L C, Wallace D R, Stevens C W. Selective opioid agonist and antagonist competition for [3H]-naloxone binding in amphibian spinal cord. Brain Res. 2000; 884 (1-2):184-191. doi:10.1016/s0006-8993(00)02967-x Nguyen K D, Mowlds D, Lopez I A, Hosokawa S, Ishiyama A, Ishiyama G. Mu-opioid receptor (MOR) expression in the human spiral ganglia. Brain Res. 2014 Nov. 24; 1590:10-9. doi: 10.1016/j.brainres.2014.09.051. Epub 2014 Sep. 30. PMID: 25278190; PMCID: PMC4437724.

Oh A K, Ishiyama A, Baloh R W. Deafness associated with abuse of hydrocodone/acetaminophen. Neurology. 2000 Jun. 27; 54(12):2345-.

Patrick S W, Dudley J, Martin P R, et al. Prescription opioid epidemic and infant outcomes. Pediatrics. 2015; 135(5): 842-850. doi:10.1542/peds.2014-3299.

Pogue B W, Samkoe K S, Hextrum S, O'Hara J A, Jermyn M, Srinivasan S, Hasan T. Imaging targeted-agent binding in vivo with two probes. J Biomed Opt. 2010 May-June; 15(3):030513. doi: 10.1117/1.3449109. PMID: 20614996; PMCID: PMC2909298.

Pradhan A A, Smith M L, Kieffer B L, Evans C J. Ligand-directed signaling within the opioid receptor family. British journal of pharmacology. 2012 November; 167(5): 960-9.

Rigby M H, Parnes L S. Profound hearing loss associated with oxycodone-acetaminophen abuse. Journal of otolaryngology-head & neck surgery=Le Journal d'oto-rhino-laryngologie et de chirurgie cervico-faciale. 2008 December; 37(6):E161.

Rzasa Lynn R, Galinkin J L. Naloxone dosage for opioid reversal: current evidence and clinical implications. *Ther Adv Drug Saf.* 2018 January; 9(1):63-88. doi: 10.1177/2042098617744161. Epub 2017 Dec. 13. PMID: 29318006; PMCID: PMC5753997.

Samkoe K S, Tichauer K M, Gunn J R, Wells W A, Hasan T, Pogue B W. Quantitative in vivo immunohistochemistry of epidermal growth factor receptor using a receptor concentration imaging approach. Cancer research. 2014 Dec. 15; 74(24):7465-74.

Schrock A, Jakob M, Wirz S, Bootz F. Sudden sensorineural hearing loss after heroin injection. European Archives of Oto-Rhino-Laryngology. 2008 May 1; 265(5):603-6.

Tichauer K M, Samkoe K S, Gunn J R, Kanick S C, Hoopes P J, Barth R J, Kaufman P A, Hasan T, Pogue B W. Microscopic lymph node tumor burden quantified by macroscopic dual-tracer molecular imaging. Nature medicine. 2014 November; 20(11):1348.

Tichauer K M, Samkoe K S, Sexton K J, Hextrum S K, Yang H H, Klubben W S, Gunn J R, Hasan T, Pogue B W. In vivo quantification of tumor receptor binding potential with dual-reporter molecular imaging. Molecular Imaging and Biology. 2012a October 1; 14(5):584-92.

Tichauer K M, Samkoe K S, Sexton K J, Gunn J R, Hasan T, Pogue B W. Improved tumor contrast achieved by single time point dual-reporter fluorescence imaging. Journal of biomedical optics. 2012b June; 17(6):066001.

Trescot A M, Datta S, Lee M, Hansen H. Opioid pharmacology. Pain physician. 2008 March; 11(2 Suppl):S133-53.

Van Gaalen F A, Compier E A, Fogteloo A J. Sudden hearing loss after a methadone overdose. European Archives of Oto-Rhino-Laryngology. 2009 May 1; 266(5):773-4.

Zubieta J K, Greenwald M K, Lombardi U, Woods J H, Kilbourn M R, Jewett D M, Koeppe R A, Schuster C R, Johanson C E. Buprenorphine-induced changes in mu-opioid receptor availability in male heroin-dependent volunteers: a preliminary study. Neuropsychopharmacology. 2000 Sep. 1; 23(3):326-34.

I claim:

1. A compound of formula (I) or a salt thereof:

(I)

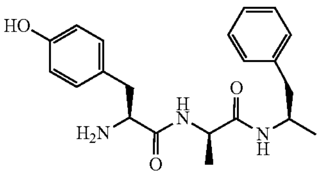

-continued

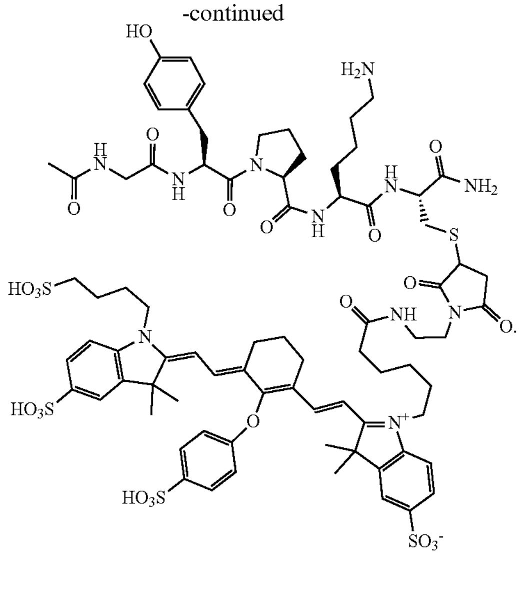

2. A composition comprising the compound of claim 1 and a carrier.

3. A method for determining occupancy level of an opioid receptor in a subject, comprising:

(a) contacting at least one probe with the subject, wherein the probe binds specifically to the opioid receptor (OR);

(b) measuring intensity of fluorescent signal emitted by the probe from inner ear of the subject; and (c) determining the occupancy level of the opioid receptor in the subject based on the fluorescence intensity, wherein the probe comprises a compound having the formula (I) or a salt thereof:

(I)

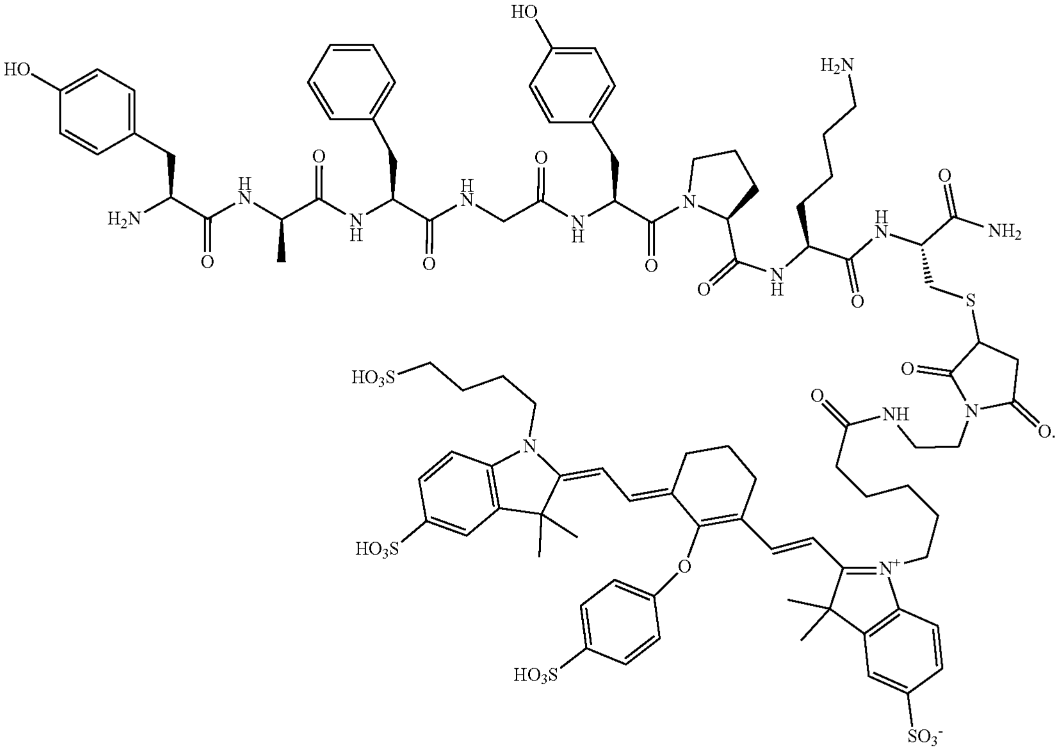

4. The method of claim 3, wherein step (b) is performed non-invasively.

5. The method of claim 3, wherein fluorescence intensity in spiral ganglion is measured in step (b).

6. The method of claim 3, wherein the fluorescence intensity is measured by using an oto-spectroscope.

7. The method of claim 3, wherein the opioid receptor is mu opioid receptor (MOR).

8. The method of claim 3, wherein the occupancy level of the opioid receptor in the subject is calculated quantitatively.

9. The method of claim 3, further comprising administering an effective amount of an opioid antagonist or a partial opioid agonist to the subject based on the occupancy level of the opioid receptor in the subject.

10. The method of claim 9, wherein the amount of the opioid antagonist or the partial opioid agonist administered is determined based on the occupancy level of the opioid receptor in the subject.

11. The method of claim 3, wherein the probe is administered into the body of the subject in step (a).

12. The method of claim 3, wherein the probe is administered by a means selected from the group consisting of nasal spray, intravenous (IV) injection, oral administration and skin patch.

13. The method of claim 3, wherein the subject has been treated with a pain medication prescribed by a physician prior to step (a).

14. The method of claim 3, wherein the method is used for preventing/treating opioid use disorder (OUD) or for monitoring response of a subject to treatment using an opioid antagonist.

15. The method of claim 3, wherein the method is used for determining the dose of pharmacotherapy in the treatment of substance use disorder.

16. The method of claim 15, wherein the substance use disorder is opioid use disorder.

17. The method of claim 15, wherein the method is used to taper down the dosage of pharmacotherapy.

18. The method of claim 15, wherein the subject is a pregnant woman with a substance use disorder and the method is used to reduce the risk of relapse in the subject.

19. The method of claim 3, wherein excitation wavelength used in step (b) ranges between 635 nm and 760 nm.

20. The method of claim 3, further comprising a step of measuring rate of internalization of the probe.

21. The method of claim 20, wherein two or more probes are used simultaneously.

22. The method of claim 20, wherein the occupancy level of the opioid receptor and the rate of internalization of the probe are used to evaluate risk of developing an opioid use disorder in the subject.

23. The method of claim 3, wherein the method is performed at point-of-care.

24. The method of claim 9, wherein an opioid antagonist is administered, and the opioid antagonist is selected from the group consisting of alvimopan, norbinaltorphimine, nalmefene, naloxone, naltrexone, methylnaltrexone, and nalorphine, and pharmaceutically acceptable salts or prodrugs thereof.

25. A kit for detecting an opioid receptor in a subject, comprising (a) a predetermined amount of compound of formula (I); and (I)

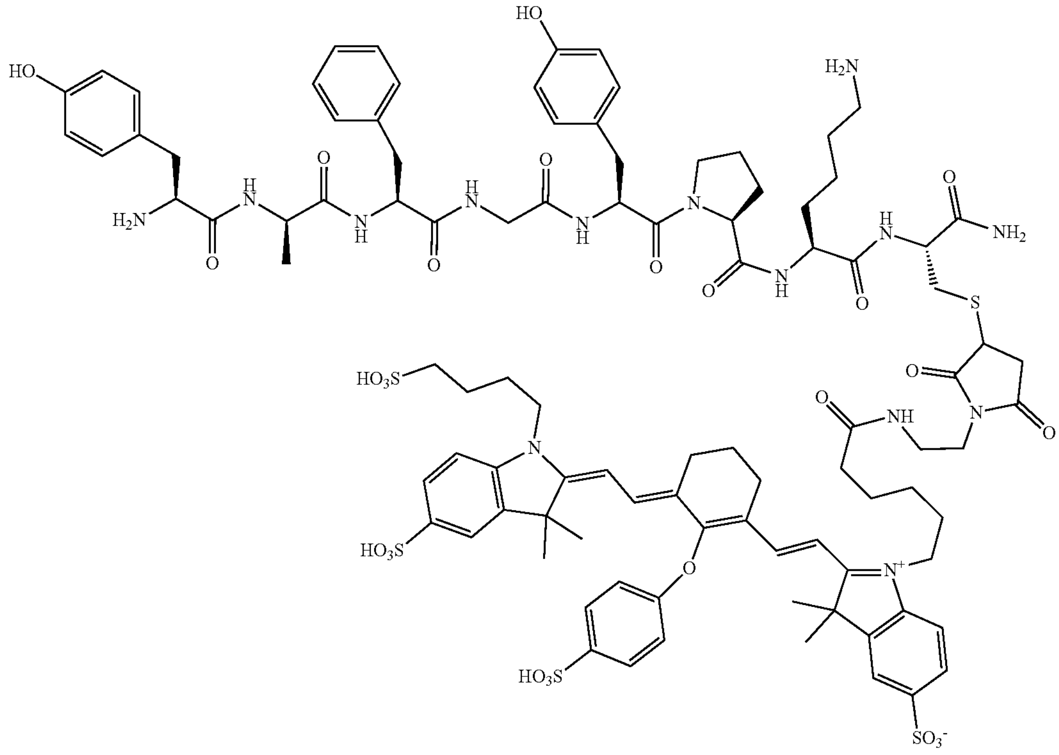

(b) instruction for using the kit.

* * * * *

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Tyr Ala Phe Gly Tyr Pro Lys Cys
1 5